United States Patent
Rose et al.

(10) Patent No.: US 10,835,506 B2
(45) Date of Patent: Nov. 17, 2020

(54) TREATMENT AND PREVENTION OF MUSCLE LOSS USING L-ORNITHINE IN COMBINATION WITH AT LEAST ONE OF PHENYLACETATE AND PHENYLBUTYRATE

(71) Applicant: OCERA THERAPEUTICS, INC., Redwood City, CA (US)

(72) Inventors: Christopher F. Rose, Montreal (CA); Franck Rousseau, Durham, NC (US)

(73) Assignee: Ocera Therapeutics, Inc., Hazelwood, MO (US)

( * ) Notice: Subject to any disclaimer, the term of this patent is extended or adjusted under 35 U.S.C. 154(b) by 0 days.

(21) Appl. No.: 15/750,009

(22) PCT Filed: Aug. 16, 2016

(86) PCT No.: PCT/US2016/047211
§ 371 (c)(1),
(2) Date: Feb. 2, 2018

(87) PCT Pub. No.: WO2017/031131
PCT Pub. Date: Feb. 23, 2017

(65) Prior Publication Data
US 2018/0221320 A1 Aug. 9, 2018

Related U.S. Application Data

(60) Provisional application No. 62/206,466, filed on Aug. 18, 2015.

(51) Int. Cl.
| | | |
|---|---|---|
| *A61K 31/192* | (2006.01) | |
| *A61P 21/00* | (2006.01) | |
| *A61P 1/16* | (2006.01) | |
| *A61K 9/00* | (2006.01) | |
| *A61K 31/198* | (2006.01) | |
| *C12Q 1/42* | (2006.01) | |
| *C12Q 1/48* | (2006.01) | |

(52) U.S. Cl.
CPC .......... *A61K 31/198* (2013.01); *A61K 9/0019* (2013.01); *A61K 31/192* (2013.01); *A61P 1/16* (2018.01); *A61P 21/00* (2018.01); *C12Q 1/42* (2013.01); *C12Q 1/48* (2013.01); *A61K 2300/00* (2013.01); *G01N 2800/085* (2013.01)

(58) Field of Classification Search
CPC .. A61K 31/192; A61K 31/198; A61K 9/0019; A61K 2300/00; A61P 1/16; A61P 21/00; G01N 2800/085
See application file for complete search history.

(56) References Cited

U.S. PATENT DOCUMENTS

| | | |
|---|---|---|
| 3,950,529 A | 4/1976 | Fischer et al. |
| 4,100,293 A | 7/1978 | Walser |
| 4,228,099 A | 10/1980 | Walser |
| 4,284,647 A | 8/1981 | Brusilow et al. |
| 4,320,146 A | 3/1982 | Walser |
| 4,352,814 A | 10/1982 | Walser |
| 4,457,942 A | 7/1984 | Brusilow et al. |
| 5,139,981 A | 8/1992 | Kurland |
| 5,405,761 A | 4/1995 | Makryaleas et al. |
| 5,571,783 A | 11/1996 | Montagne et al. |
| 5,591,613 A | 1/1997 | Makryaleas et al. |
| 5,741,524 A | 4/1998 | Staniforth et al. |
| 5,767,086 A | 6/1998 | Kauvar et al. |
| 6,083,953 A | 6/2000 | Nestor et al. |
| 6,258,849 B1 | 7/2001 | Burzynski |
| 6,451,340 B1 | 9/2002 | Arimilli et al. |
| 6,503,530 B1 | 1/2003 | Kang et al. |
| 6,514,953 B1 | 2/2003 | Armitage et al. |
| 6,768,024 B1 | 7/2004 | Watson-Straughan et al. |
| 6,943,192 B2 | 9/2005 | Burzynski |
| 8,173,706 B2 | 5/2012 | Anderson et al. |
| 8,389,576 B2 | 3/2013 | Jalan et al. |
| 8,492,439 B2 | 7/2013 | Anderson et al. |
| 8,785,498 B2 | 7/2014 | Anderson et al. |
| 8,946,473 B2 | 2/2015 | Anderson et al. |
| 9,034,925 B2 | 5/2015 | Anderson et al. |
| 9,260,379 B2 | 2/2016 | Anderson et al. |
| 9,566,257 B2 | 2/2017 | Jalan et al. |
| 9,604,909 B2 | 3/2017 | Anderson et al. |
| 10,039,735 B2 | 8/2018 | Jalan et al. |
| 10,173,964 B2 | 1/2019 | Anderson et al. |
| 2003/0105104 A1 | 6/2003 | Burzynski |
| 2003/0195255 A1 | 10/2003 | Summar |
| 2004/0152784 A1 | 8/2004 | March |
| 2004/0229948 A1 | 11/2004 | Summar et al. |
| 2005/0059150 A1 | 3/2005 | Guarino et al. |

(Continued)

FOREIGN PATENT DOCUMENTS

| | | |
|---|---|---|
| AU | 2014250643 A1 | 11/2014 |
| AU | 2015221466 A1 | 9/2015 |

(Continued)

OTHER PUBLICATIONS

Abraldes et al., "Hemodynamic Response to Pharmacological Treatment of Portal Hypertension and Long-Term Prognosis of Cirrhosis", Hepatol. 2003, 37:902-908.

(Continued)

*Primary Examiner* — Barbara P Badio
(74) *Attorney, Agent, or Firm* — Knobbe, Martens, Olson & Bear, LLP

(57) ABSTRACT

Disclosed herein are methods of treating and preventing muscle loss using ornithine in combination with at least one of phenyl acetate and phenylbutyrate.

17 Claims, 7 Drawing Sheets

(56) References Cited

U.S. PATENT DOCUMENTS

| | | |
|---|---|---|
| 2005/0182064 A1 | 8/2005 | Burzynski |
| 2006/0045912 A1 | 3/2006 | Truog |
| 2008/0119554 A1 | 5/2008 | Jalan et al. |
| 2010/0280119 A1 | 11/2010 | Anderson et al. |
| 2012/0157526 A1 | 6/2012 | Jalan et al. |
| 2012/0208885 A1 | 8/2012 | Anderson et al. |
| 2012/0259016 A1 | 10/2012 | Jalan et al. |
| 2013/0211135 A1 | 8/2013 | Anderson et al. |
| 2013/0296429 A1 | 11/2013 | Anderson et al. |
| 2014/0142186 A1 | 5/2014 | Scharschmidt et al. |
| 2014/0288327 A1 | 9/2014 | Anderson et al. |
| 2015/0133684 A1 | 5/2015 | Anderson et al. |
| 2015/0251990 A1 | 9/2015 | Anderson et al. |
| 2016/0338982 A1 | 11/2016 | Ruettimann et al. |
| 2017/0135973 A1 | 5/2017 | Wang et al. |
| 2017/0189364 A1 | 7/2017 | Jalan et al. |
| 2018/0161293 A1 | 6/2018 | Jalan et al. |
| 2018/0319736 A1 | 11/2018 | Anderson et al. |
| 2019/0070142 A1 | 3/2019 | Jalan et al. |

FOREIGN PATENT DOCUMENTS

| | | |
|---|---|---|
| CA | 2763894 | 1/2011 |
| CA | 2813563 | 4/2012 |
| CN | 1383815 A | 12/2002 |
| CN | 101010087 A | 8/2007 |
| CN | 101102816 A | 1/2008 |
| CN | 102421432 A | 4/2012 |
| CN | 102512408 A | 6/2012 |
| EP | 1 179 347 A1 | 2/2002 |
| EP | 1 334 722 A1 | 8/2003 |
| EP | 1 374 863 A1 | 1/2004 |
| EP | 1 541 141 A1 | 6/2005 |
| FR | 2113774 A1 | 6/1972 |
| GB | 965637 | 8/1964 |
| GB | 1067742 | 5/1967 |
| GB | 1080599 | 8/1967 |
| GB | 1310658 | 3/1973 |
| GB | 1507951 | 4/1978 |
| JP | 54-163518 A | 12/1979 |
| JP | 5-221858 A | 8/1993 |
| JP | 3273578 B2 | 4/2002 |
| JP | 2008-521784 | 6/2008 |
| JP | 5116479 B2 | 1/2013 |
| MX | PA03009902 A | 3/2005 |
| WO | WO 85/004805 | 11/1985 |
| WO | WO 1987/005297 | 9/1987 |
| WO | WO 97/030167 | 8/1997 |
| WO | WO 00/071151 | 11/2000 |
| WO | WO 02/034255 | 5/2002 |
| WO | WO 02/074302 | 9/2002 |
| WO | WO 03/037378 | 5/2003 |
| WO | WO 03/045372 | 6/2003 |
| WO | WO 03/086074 | 10/2003 |
| WO | WO 2004/019928 | 3/2004 |
| WO | WO 2005/053607 | 6/2005 |
| WO | WO 2005/082023 | 9/2005 |
| WO | WO 2006/056794 | 6/2006 |
| WO | WO 2006/059237 | 6/2006 |
| WO | WO 2007/077995 A1 | 7/2007 |
| WO | WO 2010/115055 | 10/2010 |
| WO | WO 2010/144498 | 12/2010 |
| WO | WO 2012/048043 | 4/2012 |
| WO | WO 2016/172112 | 10/2016 |

OTHER PUBLICATIONS

Aggarwal et al., "Predictors of Mortality and Resource Utilization in Cirrhotic Patients Admitted to the Medical ICU", Chest, 2001, vol. 119, Issue 5, pp. 1489-1497.
Al Sibae et al., "Current Trends in the Treatment of Hepatic Encephalopathy", Ther Clin Risk Manag. Jun. 2009, 5(3): 617-626.
Albrecht et al., "Contrasting effects of thioacetamide-induced liver damage on the brain uptake indices of ornithine, arginine and lysine: modulation by treatment with ornithine aspartate", Metab Brain Dis., 1996, vol. 11, Issue 3, pp. 229-237.
Albrecht et al., "Increase of the brain uptake index for L-ornithine in rats with hepatic encephalopathy", Neuro report, 1994, vol. 5, Issue 6, pp. 671-673.
Al-Hassnan et al., "The relationship of plasma glutamine to ammonium and of glycine to acid-base balance in propionic acidaemia", J. Inherit. Metab. Dis., 2003, vol. 26, pp. 89-91.
Als-Nielsen, Bodil, et al., Non-Absorbable Disaccharides for Hepatic Encephyalopathy: Systematic Review of Randomised Trials, BMJ, 2004, p. 1-6.
Anadiotis et al., "Ornithine transcarbamylase deficiency and pancreatitis", J Pediatr, 2001, vol. 138, pp. 123-124.
Anonymous, Sodium phenylbutyrate for urea cycle enzyme deficiencies. [No authors listed], Med Lett Drugs Ther., Nov. 1996, 38(988): 105-106.
Bachmann et al., "Ammonia toxicity to the brain and creatine", Molecular Genetics and Metabolism, 2004, vol. 81, pp. S52-S57.
Balata et al., "Induced hyperammonemia alters neuropsychology, brain MR spectroscopy and magnetization transfer in cirrhosis," Hepatology, 2003, vol. 4, Issue 37, pp. 931-939.
Batshaw et al., "Alternative pathway therapy for urea cycle disorders: twenty years later", J Pediatr, 2001, vol. 138, Issue 1, pp. S46-S55.
Batshaw et al., "Effect of sodium benzoate and sodium phenylacetate on brain serotonin turnover in the Ornithine transcarbamylase-deficient sparse-fur mouse", Pediatric Research, 1988, vol. 23, Issue 4, pp. 368-374.
Beale et al., "Early enteral supplementation with key pharmaconutrients improves sequential organ failure assessment score in critically ill patients with sepsis: outcome of a randomized, controlled, double blind trial,", Crit Care Med., 2008, vol. 1, Issue 36, pp. 131-144.
Berg et al., "Pharmacokinetics and cerebrospinal fluid penetration of phenylacetate and phenylbutyrate in the non-human primate", Cancer Chemother Pharmacol. (May 2001) 47(5): 385-390. Abstract Only.
Berge et al., "Pharmaceutical Salts", J Pharm Sci, 1977, vol. 66, pp. 1-19.
Berry et al., "Long-term management of patients with urea cycle disorders", J Pediatri, 2001, vol. 138, Issue 1, pp. S56-S61.
Bighley et al., "Salt Forms of Drugs and Absorption" in Encyclopedia of Pharmaceutical Technology, Eds. J. Swarbrick and J.C. Boylan, vol. 13, Marcel Dekker, Inc., New York, (1996), pp. 453-499.
Blei, Andres T., et al., Pathophysiology of Cerebral Edema in Fulminant Hepatic Failure, Journal of Hepatology, 1999, p. 771-776, vol. 31, Denmark.
Bleichner, et al., "Frequency of infections in cirrhotic patients presenting with acute gastrointestinal haemorrhage", British Journal of Surgery, 1986, vol. 73, Issue 9, pp. 724-726.
Bongers et al., "Exogenous glutamine: the clinical evidence," Crit Care Med., 2007, vol. 9 Suppl, Issue 35, pp. S545-S552.
Bosoi et al., "Minimal Hepatic Encephalopathy Renders the Brain Susceptible to Hypotension-Induced Neuronal Cell Loss in BDL Rats", A19 from the 12th Annual Canadian Association for Study of the Liver Meeting, Feb. 2016; CA J Gastroenter Hepatol. (Feb. 2016) p. 14.
Bosoi et al., Long term oral treatment of ornithine phenylacetate increases lean mass and attenuates brain edema in bile-duct ligated rats. Hepatology Oct. 2015, 62(Suppl 1):953A; Abstract 1523.
Braga et al., "Crystal Polymorphism and Multiple Crystal Forms", Struct Bond (2009) 132: 25-50 [pub online Feb. 25, 2009].
Briggs et al., "Effect of ornithine and lactate on urea synthesis in isolated hepatocytes", Biochem J, 1976, vol. 160, pp. 205-209.
Bruha et al. Effect of carvedilol on portal hypertension depends on the degree of endothelial activation and inflammatory changes, Scand. J. Gastroenterol., 41(12):1454-1463 (2006).
Brunquell et al., "Electroencephalographic findings in ornithine transcarbamylase deficiency", J Child Neurol, 1999, vol. 14, Issue 8, pp. 533-536.

(56) References Cited

OTHER PUBLICATIONS

Brusilow et al., "Amino acid acylation: A mechanism of nitrogen excretion in inborn errors of urea synthesis", Science, 1980, vol. 207, pp. 659-661.
Brusilow et al., "Treatment of episodic hyperammonemia in children with inborn errors of urea synthesis", The New England Journal of Medicine, 1984, vol. 310, Issue 25, pp. 1630-1634.
Burlina et al., "Long-term treatment with sodium phenylbutyrate in ornithine transcarbamylase-deficient patients", Molecular Genetics and Metabolism, 2001, vol. 72, pp. 351-355.
Butterworth, "Neuronal cell death in hepatic encephalopathy", Metab Brain Dis. Dec. 2007, 22(3-4): 309-320.
Butterworth, "Pathophysiology of hepatic encephalopathy: a new look at ammonia", Metab Brain Dis., 2002, vol. 17, Issue 4, pp. 221-227.
Byrn et al., "Pharmaceutical Solids: A Strategic Approach to Regulatory Considerations", Pharma Res. (1995) 12(7): 945-954.
Caira, M.R., "Crystalline Polymorphism of Organic Compounds", Topic in Current Chemistry (1998) 198: 163-208.
Callado França, et al., Five Days of Ceftriaxone to Treat Spontaneous Bacterial Peritonitis in Cirrhotic Patients, Journal of Gastroenterology, Feb. 2002, p. 119-122 vol. 37, No. 2, Springer, Japan, Abstract only.
Cavarec et al., "Molecular cloning and characterization of a transcription factor for the copia retrotransposon with homology to the BTB-Containing Lola Neurogenic Factor", Mol. Cell. Biol., 1997, vol. 17, Issue 1, pp. 482-494.
Chainuvati et al., "Ornicetil on encephalopathy. Effect of ornicetil (ornithine alpha-ketoglutarate) on encephalopathy in patients with acute and chronic liver disease", Acta Hepatogastro., 1977, vol. 24, Issue 6, pp. 434-439.
Chawla et al., "Challenges in Polymorphism of Pharmaceuticals", CRIPS (Mar. 2004) 5(1): 9-12.
Chen et al., "Continuous arteriovenous hemodiafiltration in the acute treatment of hyperammonaemia due to ornithine transcarbamylase deficiency", Renal Failure, 2000, vol. 22, Issue 6, pp. 823-836.
Chung et al., "Cirrhosis and its Complications", Harrison's Principles of Internal Medicine (16th Edition) (2005) 289, pp. 1858-1869.
Ciećko-Michalska et al., "Pathogenesis of Hepatic Encephalopathy", Gastroenter Res Practice 2012, 2012: 7 pages.
Clément et al., "Bile-ligated rats are susceptible to hypotension-induced neuronal cell loss: Implications for persisting neurological complications following liver transplantation", Posters P0012; J Hepatol. Apr. 2015, 62(Suppl. 2): S295.
Clemmesen, et al., Cerebral Herniation in Patients With Acute Liver Failure is Correlated with Arterial Ammonia Concentration, Hepatology, Mar. 1999, p. 648-653, Vo. 29, No. 3, American Association for the Study of Liver Diseases.
ClinicalTrials.gov; William Lee, Med. Uni. S.C.; "Safety Study of Ornithine Phenylacetate to Treat Patients with Acute Liver Failure (STOP-ALF)", ID #NCT01548690; Feb. 2012; 7 pages.
ClinicalTrials.gov, "Brain Muscle Axis During Treatment of Hepatic Encephalopathy With L-ornithine L-aspartate", Identifier: NCT01847651 https://clinical trials.gov/ct2/show/NCT01847651, First received: May 2, 2013, 4 pages.
Darmaun et al., "Phenylbutyrate-induced glutamine depletion in humans; effect on leucine metabolism", Am J Physiol Endocrinol Metab., 1998, vol. 274, pp. E801-E807.
Database WPI, Section Ch, Week 200331, Derwent Publications Ltd., London, GB; XP002364873 & CN 1383815 A (Liu W), Dec. 11, 2002 (Abstract Only).
Davies, et al., "L-ornithine and phenylacetate synergistically produce sustained reduction in ammonia and brain water in cirrhotic rats", Hepatology (Jul. 2009) 50(1): 155-164.
Dejong et al., "Altered glutamine metabolism in rat portal drained viscera and hindquarter during hyperammonemia", Gastroenterology, 1992, vol. 103, Issue 3, pp. 936-948.
Del Rosario et al., Hyperammonemic encephalopathy, J Clin Gastroenterol, 1997, vol. 25, Issue 4, pp. 682-684.
Desjardins et al., "Effect of portacaval anastomosis on glutamine synthetase protein and gene expression in brain, liver and skeletal muscle", Metab Brain Dis., 1999, vol. 14, Issue 4, pp. 273-280.
Dewhirst et al., "Phylogeny of the defined murine microbiota: Altered Schaedler Flora", Appl. Environ Microbiol. 1999, 65(8): 3287-3292.
Dunitz et al., "Disappearing Polymorphs", Acc Chem. Res. (1995) 28: 193-200.
Enns et al., "Survival after treatment with phenylacetate and benzoate for urea-cycle disorders,", N Engl J Med., 2007, vol. 22, Issue 356, pp. 2282-2292.
Fabbri, Andrea et al., Unresponsiveness of Hepatic Nitrogen Metabolism to Glucagon Infusion in Patients with Cirrhosis: Dependence on Liver Cell Failure, Hepatology, 1993, vol. 18, No. 1, pp. 28-35.
Garcia-Tsao, et al., Management and Treatment of Patients with Cirrhosis and Portal Hypertension: Recommendations from the Department of Veterans Affairs Hepatitis C Resource Center Program and the National Hepatitis C Program, Am J Gastroenterol, 2009, p. 1802-1829, Vo. 104.
Garden et al., "Prediction of outcome following acute variceal haemorrhage", Br J Surg., 1985, vol. 72, pp. 91-95.
Gebhardt et al., "Treatment of cirrhotic rats with L-Ornithine-L-Aspartate enhances urea synthesis and lowers serum ammonia levels", J Pharm Exp Thera., 1997, vol. 283, Issue 1, pp. 1-6.
Gonzalez-Navajas et al., "Bacterial DNA in patients with cirrhosis and sterile ascites. Its role as a marker of bacterial translocation and prognostic tool,", Rev Esp Enferm Dig., 2007, vol. 10, Issue 99, pp. 599-603.
Gordon, "Ornithine transcarbamylase deficiency: a urea cycle defect", European Journal of Paediatric Neurology, 2003, vol. 7, pp. 115-121.
Grace et al., "Prevention of initial variceal hemorrhage", Gastroenter Clin North Am., 1992, vol. 21, Issue 1, pp. 149-161.
Grant, D.J.W., "Theory and Origin of Polymorphism" Chapter 1 from Polymorphism in Pharmaceutical Solids, Brittain, Harry G. [Ed.]; Marcel Dekker, Inc., (1999) pp. 1-11.
Greenstein et al., "Studies on the Metabolism of Amino Acids and Related Compounds in Vivo. III. Prevention of Ammonia Toxicity by Arginine and Related Compounds", Archives Biochem & Biophys, (1956) vol. 64, pp. 342-354.
Grossi et al., "Amino acids mixtures in prevention of acute ammonia intoxication in dogs", Arch Surg, 1967, vol. 94, pp. 261-266.
Guillory, J.K., "Generation of Polymorphs, Hydrates, Solvates, and Amorphous" Chapter 5 from Polymorphism in Pharmaceutical Solids, Brittain, Harry G. [Ed.]; Marcel Dekker, Inc., (1999) pp. 183-226.
Häberle et al., Hyperammonamie: Ursachen, Diagnostik, Therapie, Dtsch Med Wochenschr, 2004, pp. 1430-1433, vol. 129.
Hamberg, Ole et al., Effects of an Increase in Protein Intake on Hepatic Efficacy for Urca Synthesis in Healthy Subjects and in Patients with Cirrhosis, Journal of Hepatology, 1992, pp. 237-243, Elsevier Science Publishers B.V.
Hass et al., "Detection of subclinical and overt hepatic encephalopathy and treatment control after L-Ornithine-L-Aspartate medication by magnetic resonance spectroscopy (1H-MRS)", Z Gastroenterol, 2005, vol. 43, pp. 373-378.
Häussinger et al., "Hepatic encephalopathy in chronic liver disease: a clinical manifestation of astrocyte swelling and low-grade cerebral edema?", J Hepatol., 2000, vol. 32, Issue 6, pp. 1035-1038.
Herlong et al., "The use of ornithine salts of branched-chain ketoacids in portal-systemic encephalopathy", Ann Intern Med., 1980, vol. 93, Issue 4, pp. 545-550.
Hirayama et al., [Eds], "Organic compound crystal produced handbook—Principles and know-how", Maruzen Co., Ltd., Japan; (Jul. 2008), pp. 17-23, 37-40, 45-51 and 57-65; 31 pages.
Honda et al., "Successful treatment of severe hyperammonemia using sodium phenylacetate powder prepared in hospital pharmacy", Biol. Pharm. Bull., Sep. 2002, 25(9): 1244-1246.
Hopkins Medicine (http://www.hopkinsmedicine.org/gastroenterology_hepatology/_pdfs/liver/portal_hypertension.pdf; accessed Jun. 22, 2016); 13 pages.
Hursthouse et al., "Why Do Organic Compounds Crystallise Well or Badly or Ever so Slowly? Why Is Crystallisation Nevertheless Such

(56) References Cited

OTHER PUBLICATIONS a Good Purification Technique?" Organic Process Research & Development, (2009) 13:1231-1240.

Igarashi et al., "Determination of ornithine conjugates of some carboxylic acids in birds by high-performance liquid chromatography", Chem Pharm Bull, 1992, vol. 40, Issue 8, pp. 2196-2198.

Imperial College London, Clinical Trial NCT01847651; "Brain Muscle Axis during Treatment of Hepatic Encephalopathy with L-ornithine L-aspartate", May 2013, https://clinicaltrials.gov/ct2/show/NCT01847651 retrieved Oct. 16, 2016; 4 pages.

Inoue et al., "Biochemical analysis of decreased ornithine transport activity in the liver mitochondria from patients with hyperornithinemia, hyperammonemia and homocitrullinuria", Biochim Biophys Acta., 1988, vol. 964, Issue 1, pp. 90-95.

Iyer et al., "Mouse model for human arginase deficiency", Mol Cell Biol., 2002, vol. 22, Issue 13, pp. 4491-4498.

Jalan et al., "Acute-on-chronic liver failure: pathophysiological basis of therapeutic options", Blood Purif, 2002, vol. 20, pp. 252-261.

Jalan, Intracranial Hypertension in Acute Liver Failure: Pathophysiological Basis of Rational Management, Seminars in Liver Disease, 2003, p. 271-282, vol. 23, No. 3, Thieme Medical Publisheres, Inc., New York, NY, USA.

Jalan et al., "The molecular pathogenesis of hepatic encephalopathy", The International Journal of Biochemistry & Cell Biology, 2003, vol. 35, pp. 1175-1181.

Jalan et al., "Moderate hypothermia in patients with acute liver failure and uncontrolled intracranial hypertension,", Gastroenterology, 2004, vol. 5, Issue 127, pp. 1338-1346.

Jalan et al., L-Ornithine Phenylacetate (OP): A Novel Treatment for Hyperammonemia and Hepatic Encephalopathy, Medical Hypotheses, 2007, vol. 69, Elsevier Ltd., p. 1064-1069.

Jalan et al, Treatment of Hyperammonemia in Liver Failure: A Tale of Two Enzymes, Gastroenterology, 2009, p. 2048-2051, vol. 1236.

James et al., "The conjugation of phenylacetic acid in man, sub-human primates and some non-primate species", Proc R Soc Lond B., 1972, vol. 182, pp. 25-35.

Jeyamani et al., Hepatitis E virus and acute-on-chronic liver failure,, Indian J Gastroentero., 2004, vol. 23, Issue 2, pp. 45-46.

Jiang, et al., "L-Ornithine-L-aspartate in the management of hepatic encephalopathy: A meta-analysis", Journal of Gastroenterology and Hepatology, 2008, pp. 1-6.

Jover-Cobos et al., Ornithine phenylacetate revisited; Metabolic Brain Disease 2013, 28(2): 327-331.

Kaiser et al., Ammonia and Glutamine Metabolism in Human Liver Slices: New Aspects on the Pathogenesis of Hyperammonaemia in Chronic Liver Disease, European journal of Clinical Investigation , 1988, vol. 18, pp. 535-542.

Kasumov et al., "New secondary metabolites of phenylbutyrate in humans and rats", Drug Metab Dispos., 2004, vol. 32, Issue 1, pp. 10-19.

Katayama, "Ammonia metabolism and hepatic encephalopathy", Hep. Research, 2004, vol. 30, Issue 1, pp. S71-S78.

Khan, et al., Frequency of Spontaneous Bacterial Peritonitis in Cirrhotic Patients with Ascites Due to Hepatitis C Virus and Efficacy of Cirpofloxacin in its Treatment, Gomal Journal of Medical Sciences, Jul.-Dec. 2009, p. 149-154, vol. 7, No. 2.

Khanna et al., "Non-cirrhotic portal hypertension—Diagnosis and management", J. Hepatol., Feb. 2014, 60(2): 421-441.

Kircheis et al., "Therapeutic efficacy of L-ornithine-L-aspartate infusions in patients with cirrhosis and hepatic encephalopathy: results of a placebo-controlled, double blind study,", Hepatology, 1997, vol. 6, Issue 25, pp. 1351-1360.

Kojima et al., "Effective Solid Form Selection for the Pharmaceutical Development", J Pharma Science Tech. Sep. 2008, 68(5): 344-349.

Larsen et al., "Alternative Pathway Therapy for Hyperammonemia in Liver Failure"; Hepatology, Jul. 2009, 50(1): 3-5.

Lee et al., Acute Liver Failure: Summary of a Workshop, Hepatology, Apr. 2008, vol. 47, No. 4, pp. 1401-1415.

Lee, W. M., Acetaminophen-Related Acute Liver Failure in the United States, Hepatology Research, 2008, p. S3-S8, vol. 38, Suppl. 1, The Japan Society of Hepatology.

Lee et al., "Phase 2 Comparison of a Novel Ammonia Scavenging Agent with Sodium Phenylbutyrate in Patients with Urea Cycle Disorders: Safety, Pharmacokinetics and Ammonia Control", Mol Genet Metab. Mar. 2010, 100(3): 221-228.

Linderoth et al., "Short-term prognosis of community-acquired bacteremia in patients with liver cirrhosis or alcoholism: a population-based cohort study,", Alcohol Clin Exp Res., 2006, Issue 30, pp. 636-641.

Lopez-Talavera et al. Thalidomide inhibits tumor necrosis factor alpha, decreases nitric oxide synthesis, and ameliorates the hyperdynamic circulatory syndrome in portal-hypertensive rats, Hepatology, 23(6):1616-1621 (1996).

Lucero et al., "The Role of Sarcopenia and Frailty in Hepatic Encephalopathy Management", Clin Liver Dis, Aug. 2015, 19(3): 507-528.

Lukkarinen, M. et al., Effect of Lysine Infusion on Urea Cycle in Lysinuric Protein Intolerance, Metabolism, May 2000, 49(5): 621-625.

Lukkarinen, M. et al., Oral Supplementation Corrects Plasma Lysine Concentrations in Lysinuric Protein Intolerance, Metabolism, Jul. 2003, pp. 935-938, vol. 52, No. 7, Elsevier Inc.

Macarthur et al., "Pharmacokinetics of sodium phenylacetate and sodium benzoate following intravenous administration as both a bolus and continuous infusion to healthy adult volunteers", Molecular Genetics and Metabolism, 2004, vol. 81, pp. S67-S73.

Maestri et al., "Prospective treatment of urea cycle disorders", J Pediatr., 1991, vol. 119, Issue 6, pp. 923-928.

Maestri et al., "Long-term treatment of girls with ornithine transcarbamylase deficiency", N Engl J Med., 1996, vol. 335, Issue 12, pp. 855-859.

Maev I.V. Application of L-ornitine-L-aspartate in complex therapy of hepatic encephalopathy in liver cirrhosis patients (Engl. Title) koloproktologii, 2002, No. 6, pp. 60-66.

Maier, K. P. et al., Originalien Activities of Urea-Cycle Enzymes in Chronic Liver Disease, Klinische-Wochenschrift, 1979, vol. 67, pp. 661-665, Springer-Verlag.

Matsuoka et al., "Advanced Crystallization Technology of Organic Materials—Control of Size, Morphology, Polymorph and Purity", Pharm Tech, Japan (May 2003) 19(6): 91(955)-101(965).

Mederacke et al., "High-yield and high-purity isolation of hepatic stellate cells from normal and fibrotic mouse livers", Nat Protoc. Feb. 2015, 10(2): 305-315.

Meijer et al., Nitrogen Metabolism and Ornithine Cycle Function, Physiological Reviews, Jul. 1990, vol. 70, No. 3, pp. 701-748, The American Physiological Society.

Mendenhall et al., "A new therapy for portal systemic encephalopathy", The American Journal of Gastroenterology, 1986, vol. 81, Issue 7, pp. 540-543.

Mihm et al., "Effect of L-ornithine-L-aspartate (LOLA) on neurometabolites in hepatic encephalopathy (HE)", Hepatology, 2001, vol. 34, Issue 4, pp. 543A.

Mizock et al., "Septic Encephalopathy—Evidence for altered phenylalanine metabolism and comparison with hepatic encephalopathy", Arch Intern Med, 1990, vol. 150, pp. 443-449.

Mizock, MD, FACP, Nutritional Support in Hepatic Encephalopathy, Nutrition, 1999, pp. 220-228, vol. 15, No. 3, Elsevier Science Inc.

Mizutani et al., "Hyperargininemia: Clinical course and treatment with sodium benzoate and phenylacetic acid", Brain Dev., 1983, vol. 5, Issue 6, pp. 555-563.

Mohamed et al., "Effect of toll-like receptor 7 and 9 targeted therapy to prevent the development of hepatocellular carcinoma", Liver Int. Mar. 2015, 35(3): 1063-1076.

Mohammad R.A. et al., Combination therapy for the treatment and prevention of hepatic encephalopathy; Ann Pharmacother. (Nov. 2012) 46(11): 1559-1563.

Moinard et al., "Effects of Ornithine 2-Oxoglutarateon Neutrophils in Stressed Rates: Evidence for the Involvement of Nitric Oxide and Polyamines", Clin Sci, 2002, vol. 102, Issue 3, pp. 287-295, London, England.

(56) References Cited

OTHER PUBLICATIONS

Mokhtarani, M. et al., "Urinary Phenylacetylglutamine as Dosing Biomarker for Patients with Urea Cycle Disorders", Mol Genet Metab. (Nov. 2012) 107(3): 308-314.
Mookerjee et al., "Increased gene and protein expression of the novel eNOS regulatory protein Nostrin and a variant in alcoholic hepatitis", Gastroenterology Jun. 2007, 132(7): 2533-2541.
Mookerjee et al., "Neutrophil dysfunction in alcoholilc hepatitis superimposed on cirrhosis is reversible and predicts the outcome", Hepatology, 2007, vol. 3, Issue 46, pp. 831-840.
Mouille et al., "Adaptative increase of ornithine production and decrease of ammonia metabolism in rat colonocytes after hyperproteic diet ingestion", Am J Physiol Gastroenterol Liver Physiol, 2004, vol. 287(2), pp. G344-G351.
Nance et al., "Ammonia production in germ-free Eck fistula dogs", Surgery, 1971, vol. 70, Issue 2, pp. 169-174.
Navasa et al., "Bacterial infections in liver cirrhosis,", Ital J Gastroenterol Hepatol., 1999, vol. 7, Issue 31, pp. 616-625.
Nema et al., "Excipients and Their Role in Approved Injectable Products: Current Usage and Future Directions", PDA J Pharm Sci Technol. 2011, 65(3): 287-332.
Newsholme et al., "Glutamine metabolism by lymphocytes, macrophages, and neutrophils: its importance in health and disease," J Nutr Biochem., 1999, vol. 6, Issue 10, pp. 316-324.
Newsholme, "Why is L-glutamine metabolism important to cells of the immune system in health, postinjury, surgery or infection?" J Nutr., 2001, vol. 9 Suppl, Issue 131, pp. 2515S-2522S.
Ocera Therapeutics, Inc., News Release: Ocera Announces Positive Phase 1 Results for Oral OCR-002 in Development for the Prevention of Acute Hepatic Encephalopathy; Globe Newswire; Nov. 16, 2015, 2 pages.
Ocera Therapeutics, Inc., News Release: Ocera Completes Interim Analysis of OCR-002 in Phase 2b STOP-HE Study for the Treatment of Acute Hepatic Encephalopathy; Globe Newswire; Apr. 1, 2015, 2 pages.
Ocera Therapeutics, Inc., News Release: Ocera Completes Plasma Data from Pilot Phase 1 Study for Orally-available OCR-002 in Development for the Prevention of Acute Hepatic Encephalopathy; Globe Newswire; Jan. 8, 2016, 3 pages.
Olde Damink et al., "Decreased plasma and tissue isoleucine levels after simulated gastrointestinal bleeding by blood gavages in chronic portacaval shunted rats", Gut, 1997, vol. 40, pp. 418-424.
Olde Damink et al., "Stimulated Liver and Muscle Protein Synthesis by Intravenous Isoleucine Supplementation During a Simulated Variceal Bleed in Patients with Cirrhosis of the Liver", Hepatology, Oct. 2001, AASLD Abstracts #50.
Olde Damink et al., "Interorgan ammonia and amino acid metabolism in metabolically stable patients with cirrhosis and a TIPSS", Hepatology, 2002, vol. 36, Issue 5, pp. 1163-1171.
Olde Damink et al., "Interorgan ammonia metabolism in liver failure", Neurochemistry International, 2002, vol. 41(2-3), pp. 177-188.
Olde Damink et al., "The kidney plays a major role in the hyperammonemia seen after simulated or actual GI bleeding in patients with cirrhosis", [not known], 2003, vol. 37, pp. 1277-1285.
Oria et al., "Ornithine phenylacetate prevents disturbances of motor-evoked potentials induced by intestinal blood in rats with portacaval anastomosis", J Hepatol. Jan. 2012, 56(1): 109-114.
Pauwels et al., "Systemic antibiotic prophylaxis after gastrointestinal hemorrhage in cirrhotic patients with a high risk of infection", Hepatology, 1996, vol. 24, Issue 4, pp. 802-806.
Petrowski et al., "Pharmacologic amino acid acylation in the acute hyperammonemia of propionic acidemia", Journal of Neurogenetics, 1987, vol. 4, pp. 87-96.
Plecko et al., "Partial N-acetylglutamate synthetase deficiency in a 13-year-old girl: diagnosis and response to treatment with N-carbamylglutamate", Eur J Pediatr., 1998, vol. 157, pp. 996-998.
Powell et al., "Compendium of Excipients for Parenteral Formulations", PDA J Pharm Sci Technol. 1998, 52(5): 238-311.

Puche et al., "Hepatic Stellate Sells and Liver Fibrosis", Comprehensive Physiology, 2013, 3:1473-1491.
Praphanphoj et al., "Three cases of intravenous sodium benzoate and sodium phenylacetate toxicity occurring in the treatment of acute hyperammonaemia", J Inherit Metab Dis., 2000, vol. 23, pp. 129-136.
Qiu et al., "Hyperammonemia in cirrhosis induces transcriptional regulation of myostatin by an NF-kappaB-mediated mechanism", PNAS Nov. 2013, 110(45): 18162-18167.
Qiu et al., "Hyperammonemia-mediated autophagy in skeletal muscle contributes to sarcopenia of cirrhosis", Am J Physiol Endocrinal Metab. Aug. 2012, 303: E983-993.
Rajkovic et al., "Mechanisms of abnormalities in host defences against bacterial infection in liver disease,", Clin Sci. (Lond.), 1985, vol. 3, Issue 68, pp. 247-253, London.
Ramaswamy et al., "Mouse model for human arginase deficiency", Mol Cell Biol., Jul. 2002, vol. 22, Issue 13, pp. 4491-4498.
Rees et al., "Effect of L-Ornithine-L-Aspartate on patients with and without TIPS undergoing glutamine challenge: a double blind, placebo controlled trial", Gut, 2000, vol. 47, pp. 571-574.
Riordan et al., "Treatment of hepatic encephalopathy", Curr Concepts, 1997, vol. 337, Issue 7, pp. 473-479.
Rockey et al., "Randomized, Double-Blind, Controlled Study of Glycerol Phenylbutyrate in Hepatic Encephalopathy," Hepatology (2014) 59(3): 1073-1083.
Rogers, Q. R. et al., Deficiency of Pyrroline-5-Carboxylate Synthase in the Intestinal Mucosa of the Cat, The Journal of Nutrition, 1985, pp. 146-150, vol. 115, No. 1, American Institution of Nutrition.
Rombouts et al., "Determination and Characterization of Tetraspanin-associated Phosphoinositide-4 Kinases in Primary and Neoplastic Liver Cells", In *Lipid Signaling Protocols*, 2nd Ed. [Waugh M.G.] 2015; Chapter 17, pp. 203-212.
Romero-Gómez et al., "Intestinal glutaminase activity is increased in liver cirrhosis and correlates with minimal hepatic encephalopathy", Journal of Hepatology, 2004, vol. 41, pp. 49-54.
Romero-Gómez et al., "Hepatic encephalopathy in patients with acute decompensation of cirrhosis and acute-on-chronic liver failure", J Hepatol. Feb. 2015, 62(2): 437-447.
Rose et al., "L-Ornithine-L-Aspartate in experimental portal-systemic encephalopathy: therapeutic efficacy and mechanism of action", Metabolic Brain Disease, 1998, vol. 13, Issue 2, pp. 147-157.
Rose et al., "L-Ornithine-L-Aspartate lowers plasma and cerebrospinal fluid ammonia and prevents brain edema in rats with acute liver failure", Hepatology, 1999, vol. 30, Issue 3, pp. 636-640.
Rudman, et al., Maximal Rates of Excretion and Synthesis of Urea in Normal and Cirrhotic Subjects, The Journal of Clinical Investigation, Sep. 1973, vol. 52, pp. 2241-2249.
Rukmini Devi et al., "Region-specific changes in CNS muscarinic acetylcholine receptors in a rat model of hyperammonemia", Biochem Pharmacol., 1998, vol. 56, Issue 2, pp. 237-241.
Sanyal et al., Portosystemic Encephalopathy After Transjugular Intrahepatic Portosystemic Shunt: Results of a Prospective Controlled Study, Hepatology, 1994, p. 46-55, vol. 20, No. 1, Pt. 1, The American Association for the Study of Liver Diseases.
Sanyal, A. J., Prediction of Variceal Hemorrhage in Patients with Cirrhosis, UpToDate, Inc., Website (www.uptodate.com), Jan. 2010, UpToDate.
Sarhan et al., "Effects of inhibition of ornithine aminotransferase on thioactamide-induced hepatogenic encephalopathy", Neurochem Res., 1993, vol. 18, Issue 4, pp. 539-549.
Scaglia et al., "Effect of alternative pathway therapy on branched chain amino acid metabolism in urea cycle disorder patients", Mol Genet Metabolism, 2004, vol. 81, pp. S79-S85.
Schouten et al. "Idiopathic noncirrhotic portal hypertension", Hepatology, Sep. 2011; 54(3):1071-1081.
Sears et al., "Disruption of the blood-brain barrier in hyperammonaemic coma and the pharmacologic effects of dexamethasone and difluoromethyl ornithine", J Neurosci Res., 1985, vol. 14, Issue 2, pp. 255-261.
Seiler et al., "Ornithine aminotransferase activity, liver ornithine concentration and acute ammonia intoxication", Life Sciences, 1989, vol. 45, Issue 11, pp. 1009-1020.

(56) References Cited

OTHER PUBLICATIONS

Seiler, "Ornithine aminotransferase, a potential target for the treatment of hyperammonemias", Curr Drug Targets., Sep. 2000, vol. 1, Issue 2, pp. 119-153.
Sen et al., "The pathophysiological basis of acute-on-chronic liver failure", Liver, 2002, vol. 22, Issue Suppl. 2, pp. 5-13.
Shangraw et al., Effect of Liver Disease and Transplantation on Urea Synthesis in Humans: Relationship to Acid-Base Status, AM J Physiol Gastrointest Liver Physiol, 1999, vol. 276, pp. 1145-1152.
Shawcross et al., "Ammonia impairs neutrophil phagocytic function in liver disease,", Hepatology, 2008, vol. 4, Issue 48, pp. 1202-1212.
Shawcross et al., "Dispelling myths in the teatment of hepatic encephalopathy,", Lancet, 2005, vol. 9457, Issue 365, pp. 431-433.
Shawcross et al., "Hyperammonemia impairs neutrophil function", Hepatology, 2005, vol. 42, pp. 537A.
Shen et al., "Engineering the gut microbiota to treat hyperammonemia", J Clin Invest. Jun. 2015, 125(7): 2841-2850.
Shriner, et al., "Recrystallization," in the Systematic Identification of Organic Compounds, John Wiley & Sons, Inc., New York, (1998), pp. 78-81.
Simell et al., "Waste nitrogen excretion via amino acid acylation: benzoate and phenylacetate in lysinuric protein intolerance", Pediatric Research, 1986, vol. 20, Issue 11, pp. 1117-1121.
Singh, et al., Changing Epidemiology and Predictors of Mortality in Patients With Spontaneous Bacterial Peritonitis at a Liver Transplant Unit, Clinical Microbiology and Infection, Jun. 2003, p. 531-537, vol. 9, No. 6., European Society of Clinical Microbiology and Infectious Diseases.
Smith et al., "The treatment of inborn errors of the urea cycle", Nature, 1981, vol. 291, Issue 5814, pp. 378-380.
Soláini et al., "Variations in the plasma concentration of ornithine, citrulline and arginine in acute experimental liver failure" [Article in Italian], Boll Soc Ital Biol Sper., 1981, vol. 57, Issue 7, pp. 705-710, Abstract only.
Stedman's Medical Dictionary (27th Edition, 2002).
Stewart, P. M., et al., Effects of Arginine-Free Meals on Ureagenesis in Cats, American Journal of Physiological, 1981, pp. E310-E315, vol. 241, No. 4, The American Physiological Society.
Stravitz, MD, et al., Intensive Care of Patients with Acute Liver Failure: Recommendations of the U.S. Acute Liver Failure Study Group, Critical Care Medicine, 2007, p. 2498-2508, vol. 35, No. 11, Lippincott Williams & Wilkins.
Suchy et al., Liver Disease in Children, 2nd Edition, 2001, pp. 74-77.
Sugarbaker et al., "The role of the small intestine in ammonia production after gastric blood administration", Ann Surg., 1987, vol. 206, Issue 1, pp. 5-17.
Sukhotnik et al., "Oral glutamine prevents gut mucosal injury and improves mucosal recovery following lipopolysaccharide endotoxemia in a rat," J Surg Res., 2007, vol. 2, Issue 143, pp. 379-384.
Svanberg et al., "Effects of amino acids on synthesis and degradation of skeletal muscle proteins in humans", Am J Physiol., 1996, vol. 271, Issue 4 Pt1, pp. E718-E724.
TDRdata.com, results from query of "Spontaneous Bacterial Peritonitis" in the epidemiological and references databases at www.tdrdata.com, retrieved on Jul. 27, 2010, pp. 1-7.
Teran et al., "Primary prophylaxis of variceal bleeding in cirrhosis: A cost-effectiveness analysis", Gastroenter., 1997, vol. 112, Issue 2, pp. 473-482.
Thomsen et al., "Experimental nonalcoholic steatohepatitis compromises ureagenesis, an essential hepatic metabolic function", Am J Physiol Gastrointest Liver Physiol. Jun. 2014, 307(3): G295-301.
Torres-Vega et al., "Delivery of Glutamine Synthetase Gene by Baculovirus Vectors: A Proof of Concept for the Treatment of Acute Hyperammonemia", Gene Ther., Jan. 2015, 33(1): 58-64.
Trebicka et al., Atorvastin lowers portal pressure in cirrhotic rats by inhibition of RhoA/Roh-kinase and activation of endothelial nitric oxide synthase, Hepatology, 46(1):242-253 (2007).

Tuchman, MD et al., "Episodic hyperammonemia in adult siblings with hyperornithinemia, hyperammonemia, and homocitrullinuria syndrome", Arch Neurol., 1990, vol. 47, pp. 1134-1137.
Tuchman, M., et al., Management of Inherited Disorders of Ureagenesis, The Endocrinologist, 2002, p. 99-109, vol. 12, No. 2.
Van Berlo et al., "Is increased ammonia liberation after bleeding in the digestive tract the consequence of complete absence of isoleucine in hemoglobin? A study in pigs", Hepatology, 1989, vol. 10, Issue 3, pp. 315-323.
Van Den Berg et al., "The effect of glutamine-enriched enteral nutrition on intestinal microflora in very low birth weight infants: a randomized controlled trial," Clin Nutr., 2007, vol. 4, Issue 26, pp. 430-439.
Ventura-Cots et al., Safety of ornithine phenylacetate in cirrhotic decompensated patients: an open-label, dose-escalating, single-cohort study; J Clin Gastroenter. (2013) 47(10): 881-887.
Vilstrup, H. et al., Elimination of Infused Amino Acids From Plasma of Control Subjects and of Patients With Cirrhosis of the Liver, European Journal of Clinical Investigation, 1982, vol. 12, pp. 197-202, Blackwell Scientific Publications.
Vogels et al., "L-ornithine vs L-ornithine-L-aspartate as a treatment for hyperammonemia-induced encephalopathy in rats", J Hepatology, 1997, vol. 26, Issue 1, pp. 174-182.
Walrand S., "Ornithine alpha-ketoglutarate: Could it be a new therapeutic option for sarcopenia?" J Nutr Health Aging. Aug. 2010, 14(7): 570-577.
Wasmuth et al., "Patients with acute on chronic liver failure display 'sepsis-like' immune paralysis," J Hepatol., 2005, vol. 2, Issue 42, pp. 195-201.
Wright et al., "Reduction in Ammonia with L-Ornithine, Phenylacetate (OP) but not Anti-TNF Prevents LPS Induced Brain Edema in Bile-duct Ligated Cirrhotic Rats", Abstract 773; J Hepatology (2009) 50: S283.
Ytrebø et al., "Interorgan ammonia, glutamate, and glutamine trafficking in pigs with acute liver failure," Am J Physiol Gastrointest Liver Physiol., 2006, vol. 3, Issue 291, pp. G373-G381.
Ytrebø et al., "L-Ornithine Phenylacetate Attenuates Increased Arterial and Extracellular Brain Ammonia and Prevents Intracranial Hypertension in Pigs with Acute Liver Failure", Hepatology (Jul. 2009) 50(1): 165-174.
Yudkoff et al., "In Vivo Nitrogen Metabolism in Ornithine Transcarbamylase Deficiency", J Clin. Invest, Nov. 1996, 98(9): 2167-2173.
Zetterman, Rowen K., MD, "Complications of Portal Hypertension: Hepatic Encephalopathy", Medscape (Jun. 2011) available online at www.medscape.com/viewarticle/744392; downloaded Dec. 3, 2014; 6 pages.
Zhu Q. et al., Rifaximin Attenuates Bile Duct Ligation Induced Liver Fibrosis and Portal Hypertension Through Inhibition of the TLR4 Pathway; Gastroenterology (May 2011) 140(5) Suppl 1: S903; Abstract 732.
Zhu Q. et al., Intestinal decontamination inhibits TLR4 dependent fibronectin mediated crosstalk between stellate cells and endothelial cells in liver fibrosis in mice; J Hepatol. (Apr. 2012) 56(4): 893-899.
Zieve et al., "Ammonia toxicity: comparative protective effect of various arginine and ornithine derivatives, aspartate, benzoate, and carbamyl glutamate," Metabo Brain Dis., 1986, vol. 1, Issue 1, pp. 25-35.
Zieve et al., "Conditional deficiencies of ornithine or ornithine or arginine", J Am Coll Nutr., 1986, vol. 5, Issue 2, pp. 167-176.
International Search Report and Written Opinion dated Nov. 7, 2016 for International Patent Application No. PCT/US2016/047211, International filing date Aug. 16, 2016.
Lucero et al., "The Role of Sarcopenia and Frailty in Hepatic Encephalopathy Management," Clin Liver Dis. 19 (2015) 507-528.
Nardelli et al. "Sarcopenia Is Risk Factor for Development of Hepatic Encephalopathy After Transjugular Intrahepatic Portosystemic Shunt Placement," Clinical Gastroenterology and Hepatology 2017, 15:934-936.
Kalafateli et al. "Impact of Muscle Wasting on Survival in Patients With Liver Cirrhosis," World J Gastroenterol Jun. 28, 2015; 21(24): 7357-7361.

(56) References Cited

OTHER PUBLICATIONS

Maier, "Therapie der hepatischen Enzephalopathie", Dtsch med Wschr. 1988, vol. 113, pp. 1886-1889.
Balasubramaniyan et al., "Ammonia reduction with ornithine phenylacetate restores brain eNOS activity via the DDAH-ADMA pathway in bile duct-ligated cirrhotic rats", Am J Physiol Gastrointest Liver Physiol., (published online Sep. 8, 2011) 2012, 302(1):G145-152.
Kristiansen et al., "L-Ornithine phenylacetate reduces ammonia in pigs with acute liver failure through phenylacetylglycine formation: a novel ammonia-lowering pathway", Am J Physiol Gastrointest Liver Physiol., 2014, 307(10):G1024-1031.
Ocera Therapeutics, Inc., News Release: Ocera Initiates Phase 1 Clinical Trial of Oral Drug Candidate OCR-002 for Prevention of Hepatic Encephalopathy; Globe Newswire; Sep. 16, 2015, 4 pages.
Smirnov et al., "Ammonia Neutralization and Urea Synthesis in Cardiac Muscle", Circ Res. 1974, 35(Suppl 3):58-73.
European Extended Search Report dated Mar. 18, 2019 in Application No. 16837708.3, filed Mar. 2, 2018.
Dasarathy, "Consilience in sarcopenia of cirrhosis," Journal of Cachexia, Sarcopenia and Muscle, 2012, 3:225-237, DOI 10.1007/s13539-012-0069-3.
Kumar et al., "Ammonia Lowering Reverses Sarcopenia of Cirrhosis by Restoring Skeletal Muscle Proteostasis," Hepatology, Jun. 2017, 65(6):2045-2058.
Montano-Loza et al., "Muscle wasting is associated with mortality in patients with cirrhosis," Clinical Gastroenterology and Hepatology, Feb. 2012, 10:166-173.
Bosoi et al., "Oral Ornithine Phenylacetate Attenuates Muscle Mass Loss and Prevents Hepatic Encephalopathy in BDL Rats", Abstract 23; J Clin Exper Hepatol. (Feb. 2017) 7:S18-S19.
Clément et al., "Minimal hepatic encephalopathy leads to hypotension-induced neuronal cell loss in BDL rats", Abstract 51; Hepatology (Oct. 2015) 62(Suppl 1):233A-234A.
Feuerstein et al., Cytokines, Inflammation, and Brain Injury: Role of Tumor Necrosis Factor-α. Cerebrovasc Brain Metab Rev. 1994, 6(4):341-360.
Nardelli et al., "Sarcopenia Is Risk Factor for Development of Hepatic Encephalopathy After Transjugular Intrahepatic Portosystemic Shunt Placement", Clin Gastroenterol Hepatol. 2017, 15(6):934-936.
Pahan et al., Lovastatin and Phenylacetate Inhibit the Induction of Nitric Oxide Synthase and Cytokines in Rat primary Astrocytes, Microglia, and Macrophages, J Clin Invest. BMJ Group GB, 1997, 100(11):2671-2679.
Roque et al., "32* Pro-inflammatory effects of sodium 4-phenylbutyrate in CF lung epithelial cells containing F508del-CFTR", J Cystic Fibrosis 2007, 6: S7.
Vilatoba et al., Sodium 4-phenylbutyrate protects against liver ischemia reperfusion injury; Surgery, 2005, 138(2):342-351.
Toshikuni et. Al., "Nutrition and exercise in the management of liver cirrhosis", World Journal of Gastroenterologh, Jun. 21, 2014, 20(23): 7286-7297.

p<0.01, *p<0.001 vs respective SHAM; †p<0.05, vs BDL.

*p<0.05,***p<0.001 vs respective SHAM; ††p<0.01 vs BDL

|  | SHAM | BDL | SHAM-OP | BDL-OP |
|---|---|---|---|---|
| Albumin (g/L) | 19 ± 1 | <10 ± 0*** | 17 ± 1 | 11 ± 1*** |
| Bilirubin (μmol/L) | 4 ± 2 | 178 ± 26*** | 4 ± 1 | 155 ± 38*** |
| Aspartate Aminotransferase (AST) (U/L) | 113 ± 151 | 472 ± 243*** | 65 ± 17 | 386 ± 143*** |
| Alanine Aminotransferase (ALT) (U/L) | 43 ± 5 | 75 ± 17** | 48 ± 19 | 79 ± 24** |
| Alkaline Phosphatase (U/L) | 241 ± 19 | 546 ± 143* | 213 ± 42 | 544 ± 116* | p<0.01, *p<0.001 vs respective SHAM

***p<0.001 vs respective SHAM

TREATMENT AND PREVENTION OF MUSCLE LOSS USING L-ORNITHINE IN COMBINATION WITH AT LEAST ONE OF PHENYLACETATE AND PHENYLBUTYRATE

RELATED APPLICATIONS

The present application is a U.S. national phase under 35 U.S.C. § 371 of International Application No. PCT/US2016/047211, entitled "TREATMENT AND PREVENTION OF MUSCLE LOSS USING L-ORNITHINE IN COMBINATION WITH AT LEAST ONE OF PHENYLACETATE AND PHENYLBUTYRATE," filed Aug. 16, 2016, which claims priority under 35 U.S.C. § 119(e) to U.S. Provisional Application No. 62/206,466, filed on Aug. 18, 2015. The content of these related applications is herein expressly incorporated by reference in its entirety.

BACKGROUND

Field

The present application relates to the fields of pharmaceutical chemistry, biochemistry and medicine. One aspect relates to the treatment and/or prevention of muscle loss using ornithine in combination with at least one of phenylacetate and phenylbutyrate.

Description of the Related Art

Loss of muscle is often characterized by a deterioration of muscle quantity and quality. In patients with chronic liver diseases, numerous metabolic disturbances occur which can lead to complications that impact the clinical outcome. For example, loss of muscle in patients with chronic liver diseases can lead to a decrease in functional capacity and adversely affect survival, quality of life and outcome following liver transplantation.

Various prevention, treatment and management strategies for muscle loss are currently available depending upon the severity of the symptoms. There is a need for additional therapies for treating or preventing muscle loss.

SUMMARY

Disclosed herein is a method of treating a condition of muscle loss. In some embodiments, the method comprises administering ornithine in combination with at least one of phenylacetate and phenyibutyrate to a subject in need thereof, and thereby relieving the condition. In some embodiments, the method further comprises identifying a subject suffering from a condition of muscle loss. In some embodiments, the subject has received liver transplantation.

Also disclosed herein is a method of preventing a condition of muscle loss. In some embodiments, the method comprises administering ornithine in combination with at least one of phenylacetate and phenylbutyrate to a subject in need thereof, and thereby preventing the condition. In some embodiments, the method further comprises identifying a subject is at the risk of developing a condition of muscle loss. In some embodiments, the subject is going to receive liver transplantation.

In some embodiments, the methods disclosed herein further comprises determining muscle weight, muscle circumference, lean muscle, body weight, ammonia level, function(s) of one or more liver enzymes, fat mass, lean mass, brain water content, locomotor activity, protein synthesis rate, or any combination thereof of the subject. The one or more liver enzymes can comprise, for example, albumin, bilirubin, aspartate aminotransferase, al anine aminotransferase, phosphatase alkaline, or any combination thereof. In some embodiments, the brain water content is frontal cortex water content. In some embodiments, at least one symptom of the condition of muscle loss is skeletal muscle loss. In some embodiments, at least one symptom of the condition of muscle loss is muscle mass loss. In some embodiments, the condition of muscle loss is caused by aging, disease, injury, inactivity, or any combination thereof. In some embodiments, the condition of muscle loss is sarcopenia, muscle atrophy, cachexia, muscular dystrophy, or any combination thereof. In some embodiments, the subject is suffering from chronic liver disease. In some embodiments, the chronic liver disease is cirrhosis.

In some embodiments, the treatment and/or prevention of the condition in the method disclosed herein is achieved by reducing blood ammonia, directly improving muscle metabolism, or a combination thereof.

In some embodiments, separate pharmaceutically acceptable salts of the ornithine and at least one of phenylacetate and phenylbutyrate are administered to the subject. In some embodiments, the at least one of phenylacetate and phenylbutyrate is administered as a sodium phenylacetate or sodium phenylbutyrate. In some embodiments, the ornithine is administered as a free monomeric amino acid or physiologically acceptable salt thereof. In some embodiments, the ornithine and phenylacetate is administered as ornithine phenylacetate.

In some embodiments, the administration is oral, intravenous, intraperitoneal, intragastric, or intravascular administration. In some embodiments, the administration is intravenous administration. In some embodiments, the administration is oral administration.

DETAILED DESCRIPTION

Figure 1:
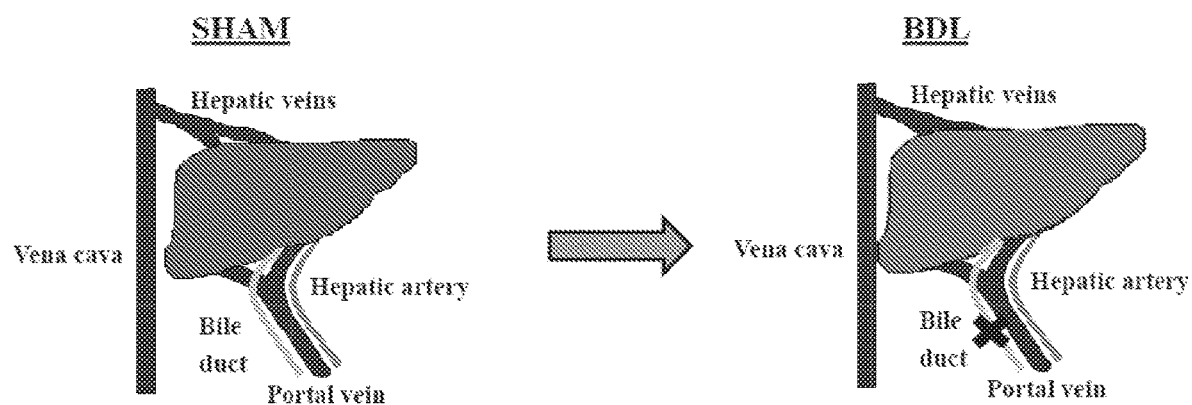
FIG. 1 is a schematic illustration of how the sham and BDL rats used in the study described in Example 4 were generated.

In the following detailed description, reference is made to the accompanying drawings, which form a part hereof. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, can be arranged, substituted, combined, and designed in a wide variety of different configurations, all of which are explicitly contemplated and make part of this disclosure.

Definitions

As used herein, a "subject" refers to an animal that is the object of treatment, observation or experiment. "Animals" include cold- and warm-blooded vertebrates and invertebrates such as fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, and apes, and, in particular, humans.

As used herein, a "patient" refers to a subject that is being treated by a medical professional, such as a Medical Doctor (i.e. Doctor of Allopathic medicine or Doctor of Osteopathic medicine) or a Doctor of Veterinary Medicine, to attempt to cure, or at least ameliorate the effects of, a particular disease or disorder or to prevent the disease or disorder from occurring in the first place.

As used herein, "administration" or "administering" refers to a method of giving a dosage of a pharmaceutically active ingredient to a vertebrate.

As used herein, a "dosage" refers to the combined amount of the active ingredients (e.g., ornithine and phenylacetate, or ornithine and phenylbutyrate)

As used herein, a "unit dosage" refers to an amount of therapeutic agent administered to a patient in a single dose.

As used herein, a "daily dosage" refers to the total amount of therapeutic agent administered to a patient in a day.

As used herein, "therapeutically effective amount" or "pharmaceutically effective amount" is meant an amount of therapeutic agent, which has a therapeutic effect. The dosages of a pharmaceutically active ingredient which are useful in treatment are therapeutically effective amounts. Thus, as used herein, a therapeutically effective amount means those amounts of therapeutic agent which produce the desired therapeutic effect as judged by clinical trial results and/or model animal studies.

As used herein, a "therapeutic effect" relieves, to some extent, one or more of the symptoms of a disease or disorder. For example, a therapeutic effect may be observed by a reduction of the subjective discomfort that is communicated by a subject (e.g., reduced discomfort noted in self-administered patient questionnaire).

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

The term "phenylacetate" as used herein, refers to the anionic form of

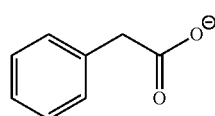

phenylacetic acid with the following chemical structure:

The term "L-ornithine phenylacetate" as used herein, refer to a compound consisting of L-ornithine cation and phenylacetate anion. It has the following chemical structure:

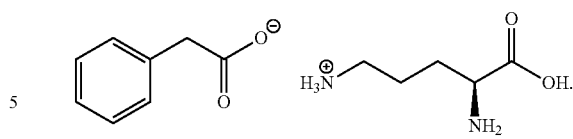

The term "phenylbutyrate" as used herein, refers to the anionic form of phenylbutyric acid with the following chemical structure:

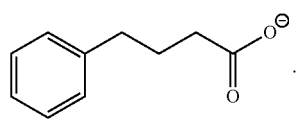 [SMILES: O=C([O-])CCCc1ccccc1]

The term "L-ornithine phenylbutyrate" as used herein, refer to a compound consisting of L-ornithine cation and phenylbutyrate anion. It has the following chemical structure:

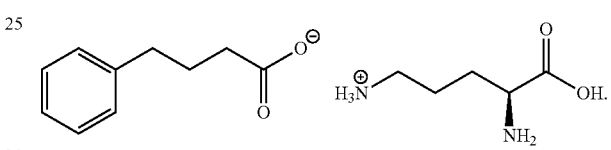

structure:
Abbreviations
BDL=bile duct ligation;
OP=ornithine, phenylacetate;
Muscle Loss Muscle loss is a condition of deterioration of muscle quantity and quality. Non-limiting symptoms of muscle loss can be loss or reduction of muscle mass, loss or reduction of lean muscle, loss or reduction of muscle weight, loss or reduction of muscle circumference, loss or reduction of fat mass, loss or reduction of lean mass, loss or reduction of muscle function, loss or reduction of muscle strength, loss or reduction of mobility, weight loss, reduction in muscle protein fractional synthesis rate (FSR), or any combination thereof. In some embodiments, at least one symptom of the condition of muscle loss is muscle mass loss or skeletal muscle loss. In some embodiment, at least one symptom of the condition of muscle loss is weight loss. In some embodiment, at least one symptom of the condition of muscle loss is loss or reduction in lean mass, loss or reduction of muscle circumference, or reduction in muscle protein fractional synthesis rate (FSR). There are a variety of causes for muscle loss. For example, the muscle loss can be caused by aging, disease (for example cancer and liver diseases), inactivity, injury (for example liver transplantation), or any combination thereof.

Some non-limiting examples of causes for muscle loss include age (e.g., age-related reduction in nerve cells responsible for sending signals from the brain to the muscles to initiate movement); a decrease in the concentration of some hormones, including but not limited to, growth hormone, testosterone, and insulin-like growth factor; a decrease in the body's ability to synthesize protein; inadequate intake of calories and/or protein to sustain muscle mass; and any combination thereof. In some embodiments, the condition of muscle loss is sarcopenia, muscle atrophy, cachexia, muscular dystrophy, muscle wasting, or any combination thereof. In patients having sarcopenia, the patients display a deterioration of muscle quantity and quality, leads to a decrease in functional capacity, adversely affecting survival, quality of life and outcome following liver transplantation. Cirrhotic patients with sarcopenia have higher ammonia levels. Without being bound by any particular theory, it is believed that the relationship between sarcopenia and hyperammonemia is bi-directional: (1) sarcopenia may reduce the subject's capacity to reduce ammonia via muscle in cirrhosis, and (2) the toxic effect of ammonia possibly affects the muscle.

Muscle loss can be a symptom or a result of an underlying condition (e.g., liver disorder), and therefore a subject may have muscle loss that is associated with a one or more conditions. In some embodiments, the muscle loss is associated with a liver disease. Non-limiting examples of liver disease include intrahepatic cholestasis (alagille syndrome, biliary liver cirrhosis), fatty liver (alcoholic fatty liver, reye syndrome), hepatic vein thrombosis, hepatolentricular degeneration, hepatomegaly, liver abscess (amebic liver abscess), liver cirrhosis (alcoholic, binary and experimental), alcoholic liver diseases (fatty liver, hepatitis, cirrhosis), parasitic (hepatic echinococcosis, fascioliasis, amebic liver abscess), jaundice (hemolytic, hepatocellular, and cholestatic), cholestasis, portal hypertension, liver enlargement, ascites, hepatitis (alcoholic hepatitis, animal hepatitis, chronic hepatitis (autoimmune, hepatitis B, hepatitis C, hepatitis D, drug induced), toxic hepatitis, viral human hepatitis (hepatitis A, hepatitis B, hepatitis C, hepatitis D, hepatitis E), Wilson's disease, granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (hepatic encephalopathy, acute liver failure), and liver neoplasms (angiomyolipoma, calcified liver metastases, cystic liver metastases, epithelial tumors, fibrolamellar hepatocarcinoma, focal nodular hyperplasia, hepatic adenoma, hepatobiliary cystadenoma, hepatoblastoma, hepatocellular carcinoma, hepatoma, liver cancer, liver hemangioendothelioma, mesenchymal hamartoma, mesenchymal tumors of liver, nodular regenerative hyperplasia, benign liver tumors (Hepatic cysts [Simple cysts, Polycystic liver disease, Hepatobiliary cystadenoma, Choledochal cyst], Mesenchymal tumors [Mesenchymal hamartoma, Infantile hemangioendothelioma, Hemangioma, Peliosis hepatis, Lipomas, Inflammatory pseudotumor, Miscellaneous], Epithelial tumors [Bile duct epithelium (Bile duct hamartoma, Bile duct adenoma), Hepatocyte (Adenoma, Focal nodular hyperplasia, Nodular regenerative hyperplasia)], malignant liver tumors [hepatocellular, hepatoblastoma, hepatocellular carcinoma, cholangiocellular, cholangiocarcinoma, cystadenocarcinoma, tumors of blood vessels, angiosarcoma, Karposi's sarcoma, hemangioendothelioma, other tumors, embryonal sarcoma, fibrosarcoma, leiomyosarcoma, rhabdomyosarcoma, carcinosarcoma, teratoma, carcinoid, squamous carcinoma, primary lymphoma]), peliosis hepatis, erythrohepatic porphyria, hepatic porphyria (acute intermittent porphyria, porphyria cutanea tarda), Zellweger syndrome).

In some embodiments, the muscle loss is associated with a chronic liver disease, for example hepatitis or cirrhosis. For example, loss of muscle mass which is characterized by a deterioration of muscle quantity and quality is frequently observed in patients suffering from cirrhosis. Cirrhosis is characterized by numerous metabolic disturbances which lead to complications that impact the clinical outcome. In some instances, the loss of muscle mass leads to decreased functional capacity adversely affecting survival, quality of life, and outcome following liver transplantation. Hyperammonemia can be a major complication of cirrhosis. Without being bound by any particular theory, it is believed that the toxic effect of ammonia can affect muscle, for example result in muscle loss. A condition of muscle loss can be, but is not necessarily, associated with liver diseases (e.g., chronic liver diseases).

Muscle loss can be determined by various conventional methods, for example measuring muscle size (for example circumference of the rectus femoris) by techniques such as ultrasound, measuring muscle resistance to an electrical current using electric impedance myography (EIM), measuring change in body weight, measuring muscle mass, measure lean mass or fat mass, measuring locomotor activity, measuring skeletal muscle fiber number, measuring muscle cross-sectional area (CSA), measuring fractional synthesis of protein (FSR) in muscle (e.g., with $D_2O$), tracking lean body mass (LBM), or any combination thereof. In some embodiments, muscle loss can be measured by tracking the lean body mass (LBM) of a subject over time.

Treatment and Prevention of Muscle Loss

Some embodiments disclosed herein include methods of treating or preventing a condition of muscle loss by co-administering to a subject in need thereof ornithine in combination with phenylacetate and/or phenylbutyrate. Some such embodiments include therapeutic treatment, and some embodiments include prophylactic treatment.

The subject in need thereof can be a patient who is suffering from a condition of muscle loss or a subject that is suspect of or at the risk of developing a condition of muscle loss. The subject may have, or may not have, symptoms of liver diseases (for example, acute liver failure or acute liver decompensation). In some embodiments, the subject does not have hyperammonemia. In some embodiments, the subject has hyperammonemia. In some embodiments, the subject does not have hepatic encephalopathy (HE). In some embodiments, the subject has HE. In some embodiments, the subject has a liver disease but is not exhibiting any significant symptoms of liver disease.

The methods disclosed herein can also comprise identifying a subject who is suffering from a condition of muscle loss or a subject that is suspect of or at the risk of developing a condition of muscle loss; and co-administering to the subject ornithine in combination with phenylacetate and/or phenylbutyrate. In some embodiments, the methods disclosed herein include acquiring knowledge of the presence of a condition of muscle loss in a subject or the risk/potential of developing a condition of muscle loss in a subject; and co-administering to the subject ornithine in combination with phenylacetate and/or phenylbutyrate.

Change in muscle loss, for example attenuation or acceleration of muscle loss can be detected, for example, by detecting loss in muscle mass, detecting change in body weight, detecting change in muscle lean mass and/or fat mass, determining change in locomotor activity, detecting change in muscle fiber number, detecting change in muscle cross-sectional area, or any combination thereof of the subject.

Some embodiments disclosed herein provide methods of treating or preventing a condition of muscle loss by co-administering to a subject in need thereof ornithine in combination with phenylacetate and/or phenylbutyrate. Some embodiments can include identifying a subject as having or at risk for developing a condition of muscle loss (e.g., sarcopenia, muscle atrophy, cachexia, or muscular dystrophy) prior to administering the ornithine in combination with phenylacetate and/or phenylbutyrate.

By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally. In another embodiment, the agents are administered through different routes, such as one being administered orally and another being administered i.v.

In some embodiments, the co-administration is useful to reduce blood ammonia level, which treat or reduce the likelihood of muscle loss. In some embodiments, muscle loss is attenuated or prevented in patients with existing chronic liver disease such as cirrhosis by the administration of the combination. Thus, in some embodiments, the combination is administered to a patient having chronic liver disease also having a condition of muscle loss.

While not being bound by any particular theory, in some embodiments, the co-administration of ornithine with phenylacetate and/or phenylbutyrate (e.g., ornithine phenylacetate (OP)) prevents or relieves the condition of portal hypertension through effects on muscle metabolism. In some embodiments, reducing muscle metabolism results in the treating or prevention of the condition of muscle loss. In some embodiments, the co-administration of ornithine with phenylacetate and/or phenylbutyrate (e.g., ornithine phenylacetate (OP)) lowers blood ammonia attenuate muscle mass loss in cirrhotic patients.

In some embodiments, the methods and composition disclosed herein can prevent or reduce loss of muscle mass (including but not limited to loss of lean muscle mass). For example, the methods and composition may prevent muscle mass loss (including but not limited to loss of lean muscle mass) from occurring. In some embodiments, the rate of muscle mass loss is reduced in a patient receiving or received treatment by at least, or at least about, 5%, 10%, 20%, 30%, 40%, 50%, 60%, 70%, 80%, or 90% as compared to the patients received no treatment. In some embodiments, the methods and composition reduce the rate of loss of muscle mass in a patient by, or by about, 5%, 10%, 20%, 30%, 40%, 50%, 60%, 70%, 80%, 90%, or a range between any two of these values as compared to the patients received no treatment. As another example, the methods and composition may reduce the final muscle mass loss (including but not limited to final loss in lean muscle mass). In some embodiments, the final muscle mass loss in the patient receiving or received treatment is at most, or at most about, 1%, 3%, 5%, 10%, 20%, 30%, 40%, 50%, 60%, 70%, 80%, or 90% of the final muscle mass loss in patients received no treatment. In some embodiments, the final muscle mass loss in the patient receiving or received treatment is, or is about, 1%, 3%, 5%, 10%, 20%, 30%, 40%, 50%, 60%, 70%, 80%, 90%, or a range between any two of these values, of the final muscle mass loss in patients received no treatment.

In some embodiments, the methods and composition disclosed herein can prevent or reduce loss of muscle weight. For example, the methods and composition may prevent muscle weight loss from occurring. In some embodiments, the rate of muscle weight loss in a patient receiving or received treatment is reduced by at least, or at least about, 5%, 10%, 20%, 30%, 40%, 50%, 60%, 70%, 80%, or 90% as compared to the patients received no treatment. In some embodiments, the methods and composition reduce the rate of loss of muscle weight in the patient receiving or received treatmet by, or by about, 5%, 10%, 20%, 30%, 40%, 50%, 60%, 70%, 80%, 90%, or a range between any two of these values as compared to patients received no treatment. As another example, the methods and composition may reduce the final muscle weight loss. In some embodiments, the final muscle weight loss in the patient receiving or received treatment is at most, or at most about, 1%, 3%, 5%, 10%, 20%, 30%, 40%, 50%, 60%, 70%, 80%, or 90% of the final muscle weight loss in patients received no treatment. In some embodiments, the final muscle weight loss in the patient receiving or received treatment is, or is about, 1%, 3%, 5%, 10%, 20%, 30%, 40%, 50%, 60%, 70%, 80%, 90%, or a range between any two of these values, of the final muscle weight loss in patients received no treatment.

In some embodiments, the methods and composition disclosed herein can prevent or reduce loss of muscle circumference. For example, the methods and composition may prevent muscle circumference loss from occurring. In some embodiments, the rate of muscle circumference loss in a patient receiving or received treatment is reduced by at least, or at least about, 5%, 10%, 20%, 30%, 40%, 50%, 60%, 70%, 80%, or 90% as compared to the patients received no treatment. In some embodiments, the methods and composition reduce the rate of muscle circumference loss in a patient receiving or received treatment by, or by about, 5%, 10%, 20%, 30%, 40%, 50%, 60%, 70%, 80%, 90%, or a range between any two of these values as compared to the patients received no treatment. As another example, the methods and composition may reduce the final muscle circumference loss. In some embodiments, the final muscle circumference loss in the patient receiving or received treatment is at most, or at most about, 1%, 3%, 5%, 10%, 20%, 30%, 40%, 50%, 60%, 70%, 80%, or 90% of the final muscle circumference loss in patients received no treatment. In some embodiments, the final muscle circumference loss in the patient receiving or received treatment is, or is about, 1%, 3%, 5%, 10%, 20%, 30%, 40%, 50%, 60%, 70%, 80%, 90%, or a range between any two of these values, of the final muscle circumference loss in patients received no treatment.

In some embodiments, the methods and composition disclosed herein can prevent or reduce loss of muscle strength. For example, the methods and composition may prevent muscle strength loss from occurring. In some embodiments, the rate of muscle strength loss in a patient receiving or received treatment is reduced by at least, or at least about, 5%, 10%, 20%, 30%, 40%, 50%, 60%, 70%, 80%, or 90% as compared to the patients received no treatment. In some embodiments, the methods and composition reduce the rate of muscle strength loss in a patient receiving or received treatment by, or by about, 5%, 10%, 20%, 30%, 40%, 50%, 60%, 70%, 80%, 90%, or a range between any two of these values as compared to patients received no treatment. As another example, the methods and composition may reduce the final muscle strength loss. In some embodiments, the final muscle strength loss in the patient receiving or received treatment is at most, or at most about, 1%, 3%, 5%, 10%, 20%, 30%, 40%, 50%, 60%, 70%, 80%, or 90% of the final muscle strength loss in patients received no treatment. In some embodiments, the final muscle strength loss in the patient receiving or received treatment is, or is about, 1%, 3%, 5%, 10%, 20%, 30%, 40%, 50%, 60%, 70%, 80%, 90%, or a range between any two of these values, of the final muscle strength loss in patients received no treatment.

In some embodiments, the methods and composition disclosed herein can prevent or reduce mobility loss. For example, the methods and composition may prevent mobility loss from occurring. In some embodiments, the rate of mobility loss in a patient receiving or received treatment is reduced by at least, or at least about, 5%, 10%, 20%, 30%, 40%, 50%, 60%, 70%, 80%, or 90% as compared to the patients received no treatment. In some embodiments, the methods and composition reduce the rate of mobility loss in the patient receiving or received treatment by, or by about, 5%, 10%, 20%, 30%, 40%, 50%, 60%, 70%, 80%, 90%, or a range between any two of these values as compared to the patients received no treatment. As another example, the methods and composition may reduce the final mobility loss. In some embodiments, the final mobility loss in the patient receiving or received treatment is at most, or at most about, 1%, 3%, 5%, 10%, 20%, 30%, 40%, 50%, 60%, 70%, 80%, or 90% of the final mobility loss in patients received no treatment. In some embodiments, the final mobility loss in the patient receiving or received treatment is, or is about, 1%, 3%, 5%, 10%, 20%, 30%, 40%, 50%, 60%, 70%, 80%, 90%, or a range between any two of these values, of the final mobility loss in patients received no treatment.

In some embodiments, the methods and composition disclosed herein can prevent or reduce weight loss. For example, the methods and composition may prevent weight loss from occurring. In some embodiments, the rate of weight loss in a patient receiving or received treatment is reduce by at least, or at least about, 5%, 10%, 20%, 30%, 40%, 50%, 60%, 70%, 80%, or 90% as compared to patients received no treatment. In some embodiments, the methods and composition reduce the rate of weight loss in a patient receiving or received treatment by, or by about, 5%, 10%, 20%, 30%, 40%, 50%, 60%, 70%, 80%, 90%, or a range between any two of these values as compared to patients received no treatment. As another example, the methods and composition may reduce the final weight loss. In some embodiments, the final weight loss in the patient receiving or received treatment is at most, or at most about, 1%, 3%, 5%, 10%, 20%, 30%, 40%, 50%, 60%, 70%, 80%, or 90% of the final weight loss in patients received no treatment. In some embodiments, the final weight loss in the patient receiving or received treatment is, or is about, 1%, 3%, 5%, 10%, 20%, 30%, 40%, 50%, 60%, 70%, 80%, 90%, or a range between any two of these values, of the final weight loss in patients received no treatment.

In some embodiments, the methods and composition disclosed herein can prevent reduction in muscle protein FSR or reduce the rate of reduction in muscle protein FSR. For example, the methods and composition may prevent the reduction in muscle protein FSR from occurring. In some embodiments, the rate of reduction in muscle protein FSR in a patient receiving or received treatment is reduced by at least, or at least about, 5%, 10%, 20%, 30%, 40%, 50%, 60%, 70%, 80%, or 90% as compared to patients received no treatment. In some embodiments, the methods and composition reduce the rate of reduction in muscle protein FSR in a patient receiving or received treatment by, or by about, 5%, 10%, 20%, 30%, 40%, 50%, 60%, 70%, 80%, 90%, or a range between any two of these values as compared to the patients received no treatment.

Salts

In some embodiments, the ornithine and phenylacetate or phenylbutyrate are administered as pharmaceutically acceptable salts. The term "pharmaceutically acceptable salt" refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable salts can also be formed using inorganic and organic bases. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as $Li^+$, $Na^+$, $K^+$, $Mg^{2+}$ and $Ca^{2+}$ and the like. Organic bases from which salts can be derived include, for example, primary, secondary, and tertiary amities, substituted amines including naturally occurring substituted amities, cyclic amines, basic ion exchange resins, and the like, specifically such as isopropylamine, trimethylamine, diethylamine, triethylamine, tripropylamine, and ethanolamine. Many such salts are known in the art, as described in WO 87/05297 published Sep. 11, 1987 (incorporated by reference herein in its entirety).

In some embodiments, ornithine is administered as the ornithine HCl salt. In some embodiments, phenylacetate or phenylbutyrate is administered as their sodium salts. In some embodiments, omithine and phenylacetate or phenylbutyrate are administered as salts of each other (e.g., omithine phenylacetate).

Pharmaceutical Compositions and Methods of Administration

The ornithine (e.g., L-ornithine) and phenylacetate or phenylbutyrate may be administered separately or in a single dosage form. In one embodiment, the combination is administered as the ornithine phenylacetate salt or as a solution of the ornithine phenylacetate salt.

Different forms of composition of ornithine in combination with at least one of phenylacetate (or phenyl acetate salts) and phenylbutyrate have been described in U.S. Patent Publication Nos. US2008/0119554 and US2010/0280119, which are hereby incorporated by reference in their entireties. In some embodiments, ornithine and phenylacetate is present and/or administered as ornithine phenyl acetate or physiologically acceptable salt thereof. In some embodiments, ornithine is present and/or administered as a free monomeric amino acid or physiologically acceptable salt thereof In some embodiments, at least one of phenylacetate and phenylbutyrate is present and/or administered as a sodium phenylacetate or sodium phenylbutyrate. In some embodiments, a physiologically acceptable salt of ornithine and a physiologically acceptable salt of at least one of phenylacetate and phenylbutyrate are administered to the subject.

As disclosed herein, the ornithine and the phenylacetate and/or phenylbutyrate can be formulated for administration in a pharmaceutical composition comprising a physiologically acceptable surface active agents, carriers, diluents, excipients, smoothing agents, suspension agents, film forming substances, coating assistants, or a combination thereof. In some embodiments, the ornithine and the phenylacetate and/or phenylbutyrate are formulated for administration with a pharmaceutically acceptable carrier or diluent. The ornithine and the phenylacetate and/or phenylbutyrate can be formulated as a medicament with a standard pharmaceutically acceptable carrier(s) and/or excipient(s) as is routine in the pharmaceutical art. The exact nature of the formulation will depend upon several factors including the desired route of administration. Typically, ornithine and the phenylacetate and/or phenybutyrate are formulated for oral, intravenous, intragastric, intravascular or intraperitoneal administration. Standard pharmaceutical formulation techniques may be used, such as those disclosed in Remington's The Science and Practice of Pharmacy, 21st Ed., Lippincott Williams & Wilkins (2005), incorporated herein by reference in its entirety.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al, (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions usefill as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions include compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et at, Pharmaceutical Dosage Forms: Tablets (1989); and Ansel, Introduction to Pharmaceutical Dosage Forms 8th Edition (2004).

Various oral dosage forms can be used, including such solid forms as tablets, capsules, and granules. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carriers suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, PDA J Pharm Sci and Tech 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, dosages may be between about 0.1 mg/kg and 4000 mg/kg body weight, preferably between about 80 mg/kg and 1600 mg/kg body weight. Alternatively dosages may be based and calculated upon the surface area of the patient, as understood by those of skill in the art.

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on many factors including the subject being treated, the severity of the affliction, the manner of administration, the judgment of the prescribing physician. The compound or combination of compounds disclosed herein may be administered orally or via injection at a dose from 0.1 mg/kg to 4000 mg/kg of the patient's body weight per day. The dose range for adult humans is generally from 1 g to 100 g/day. Tablets or other forms of presentation provided in discrete units may conveniently contain an amount of the compound or combination of compounds disclosed herein which is effective at such dosage or as a multiple of the same, for instance, units containing 1 g to 60 g (for example, from about 5 g to 20 g, from about 10 g to 50 g, from about 20 g to 40 g, or from about 25 g to 35 g). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity. A typical dose of ornithine, or of phenylacetate or phenylbutyrate can be from 0.02 g to 1.25 g per kg of body weight, for example from 0.1 g to 0.5 g per kg of body weight, depending on such parameters. In some embodiments, a dosage of ornithine, or of phenylacetate or phenylbutyrate can be from 1 g to 100 g, for example, from 10 g to 80 g, from 15 g to 60 g, from 20 g to 40 g, or from 25 g to 35 g. In some embodiments, the ornithine and phenylacetate/phenylbutyrate can be administered in a weight ratio from 10:1 to 1:10, for example, from 5:1 to 1:5, from 4:1 to 1:4, from 3:1 to 1:3, from 2:1 to 1:2, or about 1:1. A physician will be able to determine the required dosage of ornithine and of phenylacetate or phenylbutyrate for any particular subject.

The exact formulation, route of administration and dosage for the pharmaceutical compositions of the compound or combination of compounds disclosed herein can be chosen by the individual physician in view of the patient's condition. (See, e.g., Fingl et al. 1975, in "The Pharmacological Basis of Therapeutics," which is hereby incorporated herein by reference, with particular reference to Ch. 1). Typically, the dose range of the composition administered to the patient can be from about 0.1 to about 4000 mg/kg of the patient's body weight. The dosage may be a single one or a series of two or more given in the course of one or more days, as is needed by the patient. In instances where human dosages for compounds have been established for at least some condition, the present disclosure will use those same dosages, or dosages that are between about 0.1% and about 5000%, more preferably between about 25% and about 1000% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. In cases of administration of a pharmaceutically acceptable salt, dosages may be calculated as the free base. In some embodiments, the composition is administered 1 to 4 times per day. Alternatively the compositions of the compound or combination of compounds disclosed herein may be administered by continuous intravenous infusion, preferably at a dose of each active ingredient up to 100 g per day. As will be understood by those of skill in the art, in certain situations it may be necessary to administer the compound disclosed herein in amounts that exceed, or even far exceed, the above-stated, preferred dosage range in order to effectively and aggressively treat particularly aggressive diseases or infections. In some embodiments, the compound or combination of compounds disclosed herein will be administered for a period of continuous therapy, for example for a week or more, or for months or years.

In some embodiments, the dosing regimen of the compounds) or combination of compounds disclosed herein is administered for a period of time, which time period can be, for example, from at least about 1 week to at least about 4 weeks, from at least about 4 weeks to at least about 8 weeks, from at least about 4 weeks to at least about 12 weeks, from at least about 4 weeks to at least about 16 weeks, or longer. The dosing regimen of the compound(s) or combination of compounds disclosed herein can be administered three times a day, twice a day, daily, every other day, three times a week, every other week, three times per month, once monthly, substantially continuously or continuously.

EXAMPLES

Embodiments of the present application are disclosed in further detail in the following examples, which are not in any way intended to limit the scope of the present disclosure.

Example 1

In Vivo Effect in BDL Rats

Chronic liver disease (CLD) was induced in rats following 6-week bile-duct ligation (BDL). Four experimental groups were tested; 1) Sham; 2) BDL; 3) Sham+OP; and 4) BDL+OP. One week following BDL, rats were orally administered (gavage) OP (1g/kg) daily for 5 weeks. Body weight, fat and lean mass (ECHOMRI), blood ammonia, cerebral edema (specific gravity method), fractional synthesis of protein (FSR) in muscle (with D2O) and locomotor activity (day/night) were measured.

At the end of the 6-weeks experiment, BDL rats demonstrated a 4-fold increase in blood ammonia vs Sham-operated controls. This increase was reduced by 40% in OP-treated BDL rats. BDL rats gained less body weight compared to sham-operated controls (body weight of 360.2 g±13.6 vs 476.8 g±10.38; p<0.001) which was accompanied with a lower gain of lean mass and a lower muscle FSR. OP-treated BDL rats showed a significant increase in body weight (429.6 g±117.9; p<0.001 vs BDL) with a significant higher lean mass (303.1 g±10.7 in BDL+OP vs 264.4 g±10.5 in BDL, p<0.01). Fat mass remained unchanged between the treated and untreated BDL groups. OP treatment normalized brain water content in BDL rats. In contrast, OP-treatment reduced muscle FSR in SHAM animals, but not in BDL rats. Locomotor activity in BDL rats was reduced compared with sham-operated controls but no significant change was found between BDL+OP and SHAM+OP.

These results demonstrate efficient ammonia-lowering effect, as well as a protective effect on the development of brain edema and muscle mass loss, of an oral formulation of OP. In addition, these data supports the use of ornithine phenylacetate in the treatment (including prevention) of muscle loss.

Example 2

Treatment of Sarcopenia in Rats

This example is to determine whether treatment with L-ornithine phenylacetate combinations (OP) decreases age-related muscle loss in rats.

The Fisher 344×Brown Norway (FBN) rat model has been recommended by the National Institute on Aging (NIA) for age-related research. In some instances, the rats suffer from chronic liver disease. Muscle mass, fiber number, and muscle cross-sectional area (CSA) in young (e.g., 5 months), middle age (e.g., 18 months), and old (e.g., 36 months) FBN hybrid rats are measured. Significant muscle mass loss, a reduction in muscle CSA, and muscle fiber loss are expected in, for example, the quadriceps muscles of the aged rat.

OP is administered, for example orally, to young, middle age, and old FBN hybrid rats. It is expected that the administration of OP is effective in reducing muscle mass loss in middle age and/or old FBN hybrid rats.

Example 3

Treatment of Cachexia in Rats

This example is to determine whether treatment with L-ornithine phenylacetate combinations (OP) treat cachexia in rats.

A rat model of cachexia, for example the $Apc^{Min/+}$ rats, is used. In some instances, the rats suffer from chronic liver disease. Muscle mass, fiber number, and muscle cross-sectional area (CSA) of the $Apc^{Min/+}$ rats are measured before and after being administered with OP. It is expected that the administration of OP is effective in reducing muscle mass loss in the $Apc^{min/+}$ rats.

Example 4

Prevention of Muscle Mass Loss in Cirrhotic Rats

Figure 2A:
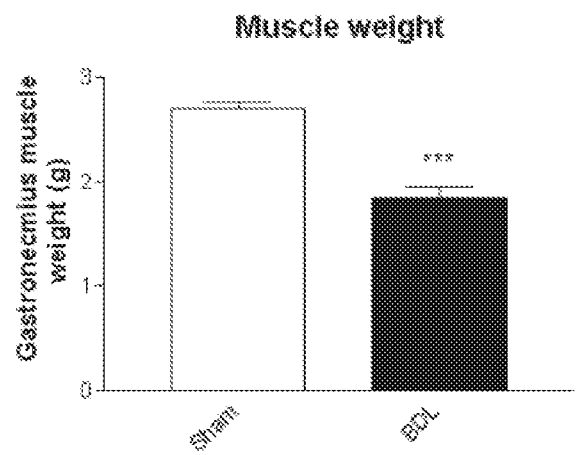
FIGS. 2A-C show muscle weight, muscle circumference and lean muscle of sham and BDL rats.
Figure 2B:
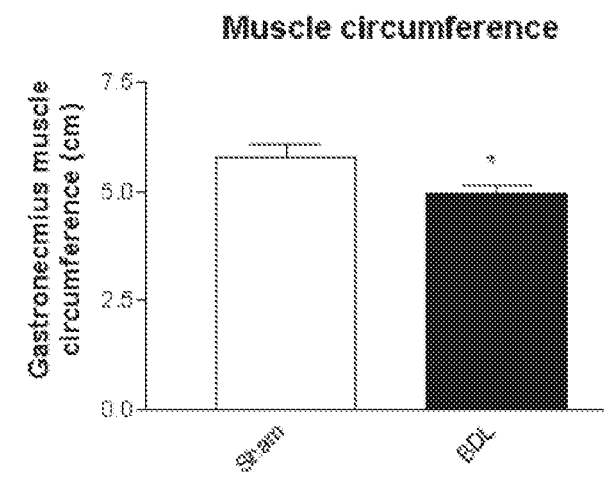
Figure 2C:
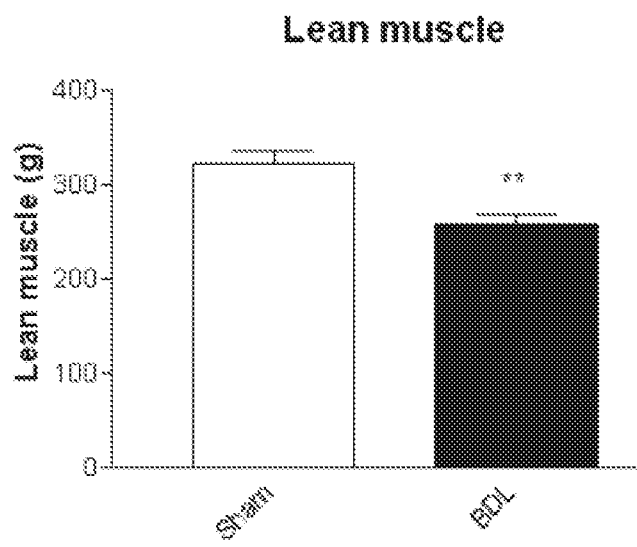

In the study described in this Example, 6-week bile-duct ligated (BDL) rat model was used. To generate the animal model, cirrhosis was induced in male Sprague-Dawley rats (200-225 g) (Charles River, St-Constant, QC) following bile-duct ligation. The characteristics of the BDL rats are: jaundice, ascites, liver dysfunction, brain edema, hyperammonemia, and minimal HE. As shown in FIGS. 2A-C, the BDL rats also showed loss in gastrocnemius muscle mass and decrease in circumference.

As previously described, rats were anaesthetized with isoflurane, and the common bile duct ligated and resected under a dissecting microscope. Sham-operated control rats, matched for weight, were similarly anaesthetized; a laparotomy was performed and the bile duct was isolated (Rose et al. Gastroenterology 117:640-644 (1999); Bosoi et al. Hepatology 53:1995-2002 (2011); Bosoi et al. Free Radic Biol Med 52:1228-1235 (2012)). Rats were maintained under controlled conditions (22° C., 12 h:12 h dark-light cycle) with free access to their food and water. One week following the BDL surgery, rats were treated orally daily with ornithine phenylacetate (OP; 1 g/kg) by gavage for 5 weeks. Experiments were conducted following the guidelines of the Canadian Council on Animal Care. Four experimental groups of animals were tested: (1) sham; (2) BDL, (3) sham+OP, and (4) BDL+OP.

Figure 3A:
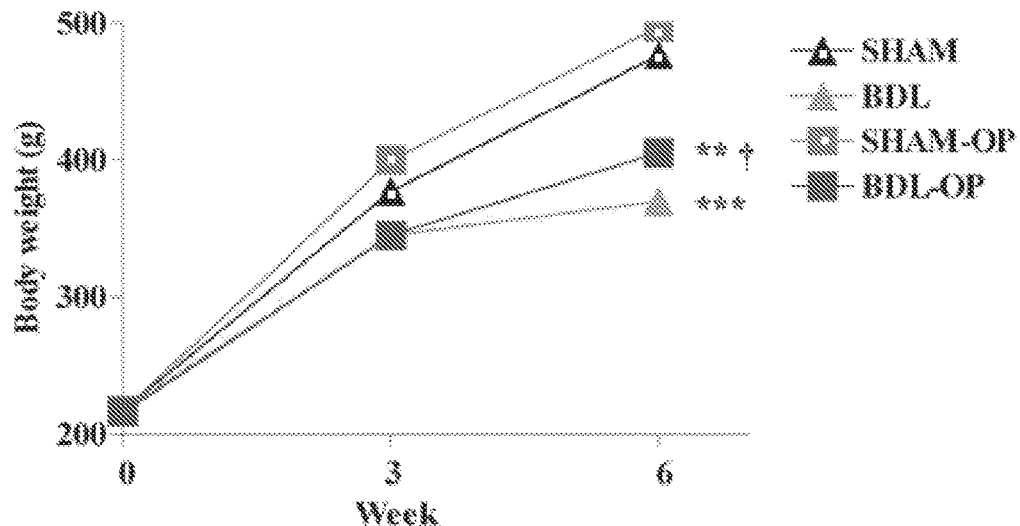
FIGS. 3A-H show body weight, ammonia level, liver enzyme function, fat mass, lean mass, frontal cortex water content, locomotor activity, and muscle protein fractional synthesis rate (FSR) in all four experimental groups (including sham, BDL, sham-OP, and BDL-OP groups)

Body weight of the rats was measured every day for the 6 week after BDL surgery (including the 5-week treatment) using an electronic scale. As shown in FIG. 3A, BDL rats gained less body weight compared to sham-operated controls ($p<0.001$). At 6 weeks, OP-treated BDL rats showed a significant increase in body weight ($P<0.05$ vs BDL rats).

Figure 3B:
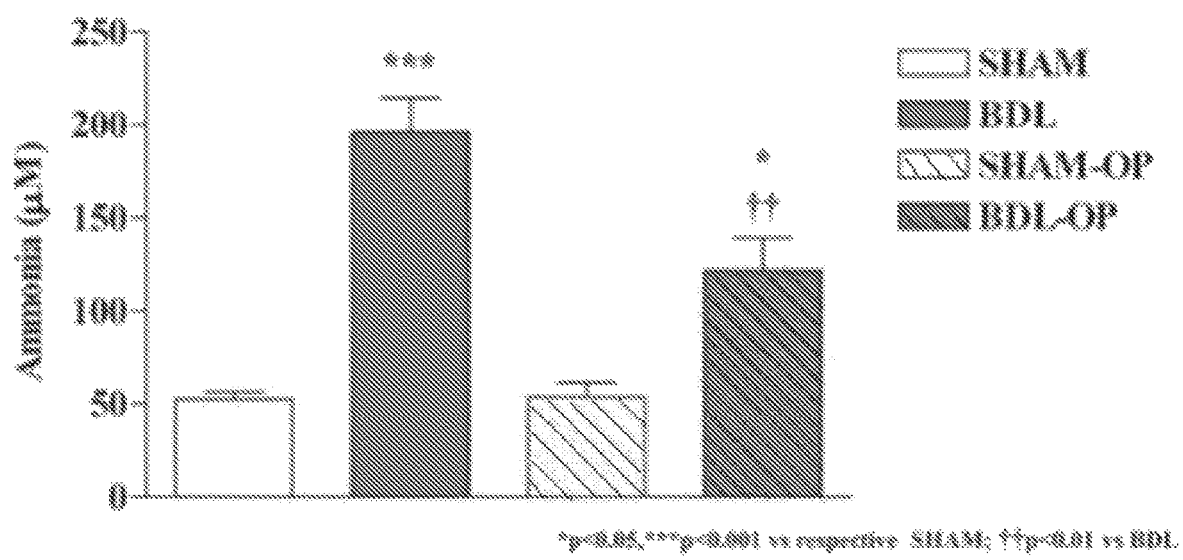
Figures 3C, 3D:
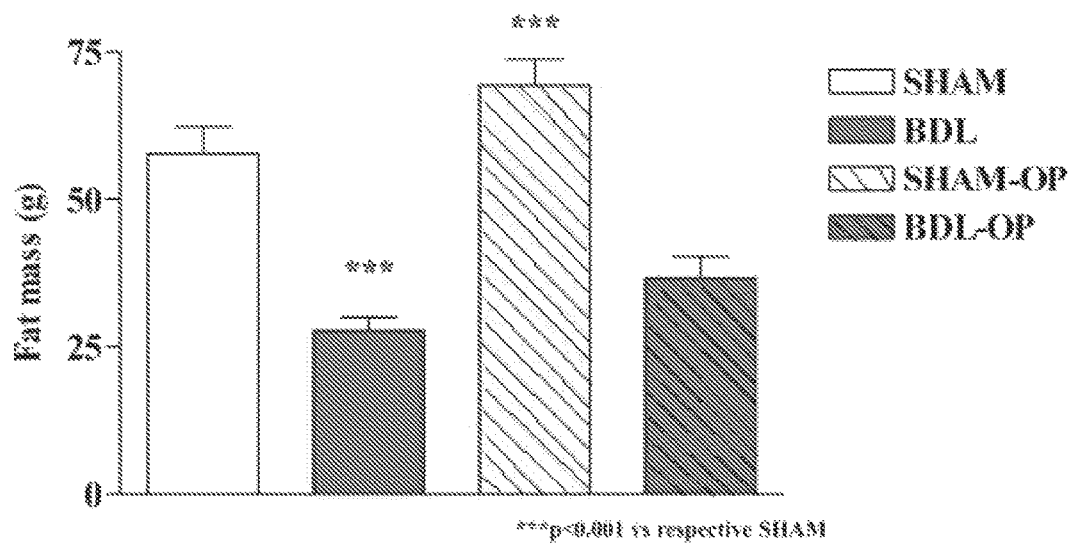

6-week post BDL surgery, blood ammonia and liver enzymes of the rats were measured. Plasmatic ammonia, albumin, bilirubin, aspartate aminotransferase, alanine aminotransferase, phosphatase alkaline levels in SHAM, BDL and BDL treated with OP were measured using routine biochemistry techniques. To measuring ammonia, commercial kit based on the reaction of α-ketoglutarate and reduced nicotinamide adenine dinucleotide phosphate in the presence of L-glutamate dehydrogenase was used. The results for blood ammonia are shown in FIG. 3B which shows that ammonia increased 4-fold in BDL rats vs. sham-operated rats and a significant increase was observed in OP-treated BDL rats ($p<0.01$ vs. BDL rats). The results of liver enzymes are shown in FIG. 3C.

Figure 3E:
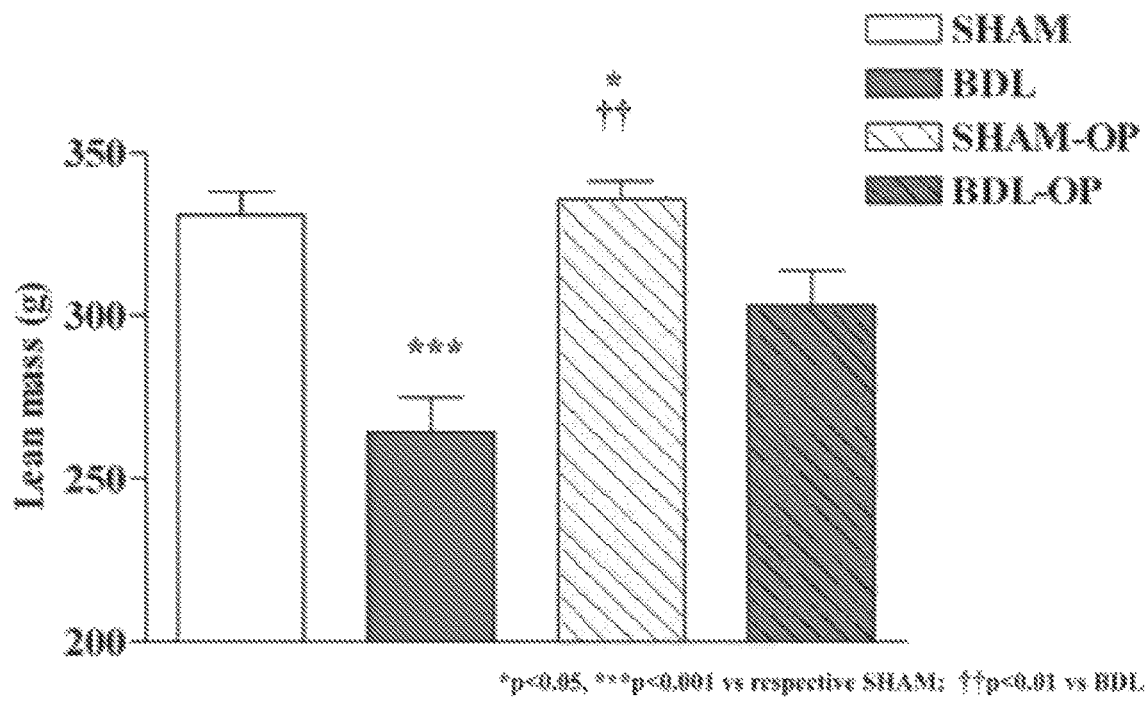

Body mass composition in terms of lean and fat mass was also assessed in conscious rats (full body) by in vivo scanning and magnetic resonance imaging (ECHOMRI-100 Body Composition Analyzer) 6 weeks after the surgeries, according to the manufacturer's protocol. The instrument for composition analysis creates contrast between soft tissues by taking advantage of the differences in relaxation times of the hydrogen proton spins in different environments. Radio pulses cause protons to spin and emit radio signals which are then received and analysed. The amplitude, duration, and spatial distribution of these signals are related to properties of the material scanned. The high contrast between fat, muscle tissue, and free water is further enhanced by application of define composed radio pulses sequences similarly as described in Nixon et al. Obesity (Silver Spring) 18:1652-1659 (2010). The results are shown in FIG. 3D (fat mass) and FIG. 3E (lean mass). As shown in FIG. 3E, BDL rats demonstrated a lower gain of lean mass compared to sham-operated controls. OP-treated BDL rats showed a significant higher lean mass ($p<0.01$ vs BDL rats). As shown in FIG. 3D, fat mass decreased in BDL rats compared to sham-operated controls and remained unchanged between the treated and untreated BDL groups.

Figure 3F:
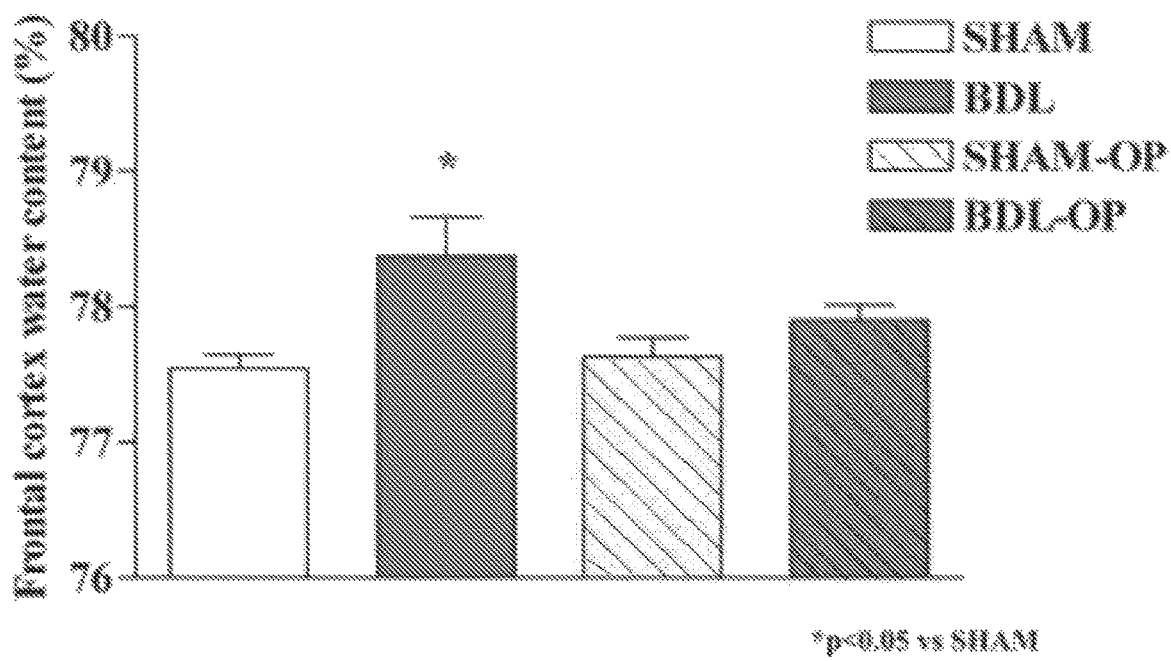

Brain water content of the animals was measured using the sensitive densitometry technique, as previously described in Bosoi et al, 2012. Briefly, after the animal was sacrificed frontal cortex was freshly dissected at 4° C. and cut into 2 mm3 pieces. Tissue pieces were placed in density gradient columns and equilibrium point was recorded after 2 minutes. Columns were made with different kerosene and bromobenzene mixtures and precalibrated with $K_2SO_4$ solutions of known densities. 8 samples measurements were averaged in each rat. Water content was calculated based on tissue density, according to the formula described by Marmarou et al., J Neurosurg. 49(4):530-537 (1978). The results of brain edema are shown in FIG. 3F. As shown in FIG. 3F, frontal cortex water content significantly increased in BDL rats ($p<0.05$ vs SHAM) and normalized following OP treatment.

Figure 3G:
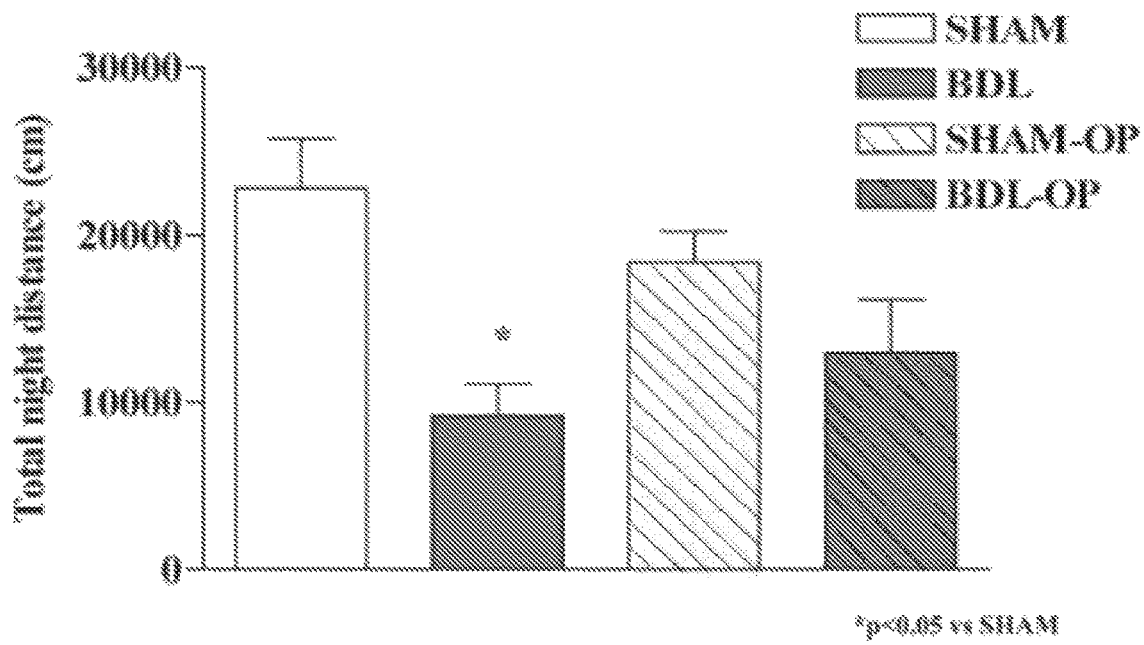

Locomotor activity of the animals was assessed using an infrared beam computerized auto-track system (Accuscan). Rats were individually placed in plexiglas cages for 6 hours before beginning to record activity. Distance travelled during the night (active) and day (inactive) period was recorded for 24 hours. As shown in FIG. 3G, locomotor activity in BDL rats was reduced compared with sham-operated controls ($p<0.05$) but no significant change was found between SHAM and BDL OP-treated rats.

Figure 3H:
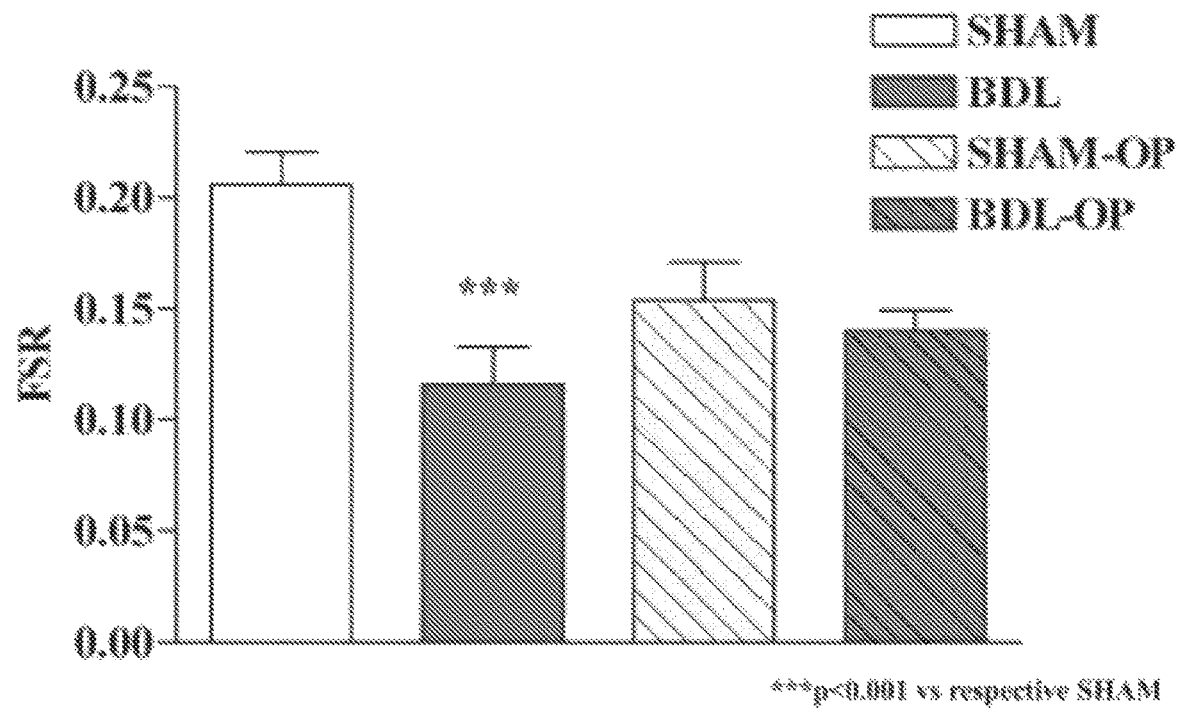

Rate of protein synthesis was quantified as the fractional and absolute protein synthesis rates in the dissected and homogenized muscle and other organs including the brain (frontal cortex), heart, intestine, kidney and liver, using the modified phenylalanine tracer pulse method described in Zhang et al. Am J Physiol Endocrinol Metab 283:E753-764 (2002) and Dasarathy et al. J Hepatol 54:915-921 (2011). In brief, rats were given a small dose (0.5 mg/100 g body weight) of L-[ring-$^2H_5$]phenylalanine ip at t=0 minute, L-[1-$^{13}C$]Phenylalanine ip at t=30 minutes and L-[15N] Phenylalanine ip at t=60 minutes. At t=65 minutes, the rats were killed and blood and tissue collected. The calculation of the fractional protein synthesis was done by using the enrichment in tissue protein samples of L-[ring-$^2H_5$]phenylalanine, divided by the average enrichment in plasma (from area under the curve calculation of the curve, constructed from the three different phenylalanine isotopes). The enrichment of phenylalanine in plasma and tissue hydrolysates was measured by liquid chromatography coupled to mass spectrometry (LC-MS/MS) as described in Engelen et al. J Cyst Fibros 12; 445-453 (2013) and Luiking et al. Clin Sci 128:57-67 (2015), The results are shown in FIG. 3H (FSR: fractional protein synthesis rate). As shown in FIG. 3H, BDL rats demonstrated a lower muscle FSR compared to sham-operated controls, and OP-treatment reduced muscle FSR in sham-operated animals, but not in BDL rats.

In the statistical analysis, data were expressed as mean±standard error of the mean (SEM). Significance of difference was tested with unpaired t test or ANOVA followed by Bonferroni post-test using GraphPad Prism4 (La Jolla, Calif., USA). Probability values of $p<0.05$ were considered statistically significant.

This example shows that the oral OP formulation efficiently lowers ammonia, preserves muscle mass and functions, improves locomotor activity, and protects against the development of brain edema in rats with cirrhosis.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein, including patents, patent applications, papers, text books, and the like, and the references cited herein, to the extent that they are not already, are hereby incorporated by reference in their entirety. In the event that one or more of the incorporated literature and similar materials differ from or contradict this application, including but not limited to defined terms, term usage, described techniques, or the like, this application controls.

What is claimed is:

1. A method of treating a condition of muscle loss, comprising administering ornithine in combination with at least one of phenylacetate and phenylbutyrate to a subject suffering from a condition of muscle loss, and thereby relieving the muscle loss condition.

2. The method of claim 1, wherein the subject has received liver transplantation.

3. The method of claim 1, wherein the subject is going to receive liver transplantation.

4. The method of claim 1, further comprising determining muscle weight, muscle circumference, lean muscle, body weight, ammonia level, function(s) of one or more liver enzymes, fat mass, lean mass, brain water content, locomotor activity, protein synthesis rate, or any combination thereof of the subject.

5. The method of claim 4, wherein the one or more liver enzymes comprise albumin, bilirubin, aspartate aminotransferase, alanine aminotransferase, phosphatase alkaline, or any combination thereof.

6. The method of claim 4, wherein the brain water content is frontal cortex water content.

7. The method of claim 1, at least one symptom of the condition of muscle loss is skeletal muscle loss or muscle mass loss.

8. The method of claim 1, wherein the condition of muscle loss is caused by aging, disease, injury, inactivity, or any combination thereof.

9. The method of claim 1, wherein the condition of muscle loss is sarcopenia, muscle atrophy, cachexia, muscular dystrophy, or any combination thereof.

10. The method of claim 1, wherein the subject is suffering from chronic liver disease.

11. The method of claim 10, wherein the chronic liver disease is cirrhosis.

12. The method of claim 1, wherein the treatment of the condition comprises reducing blood ammonia, directly improving muscle metabolism, or a combination thereof.

13. The method of claim 1, wherein separate pharmaceutically acceptable salts of the ornithine and at least one of phenylacetate and phenylbutyrate are administered to the subject.

14. The method of claim 13, wherein the at least one of phenylacetate and phenylbutyrate is administered as a sodium phenylacetate or sodium phenylbutyrate.

15. The method of claim 1, wherein the ornithine is administered as a free monomeric amino acid or physiologically acceptable salt thereof.

16. The method of claim 1, wherein the ornithine and phenylacetate is administered as ornithine phenylacetate.

17. The method of claim 1, wherein the administration is oral, intravenous, intraperitoneal, intragastric, or intravascular administration.

* * * * *